US006352852B1

(12) United States Patent
Freeman et al.

(10) Patent No.: US 6,352,852 B1
(45) Date of Patent: Mar. 5, 2002

(54) METHOD FOR THE PURIFICATION OF HUMAN PLATELET HEPARANASE

(75) Inventors: Craig Geoffrey Freeman, Rivett; Christopher Richard Parish, Campbell, both of (AU)

(73) Assignee: The Australian National University, Acton (AU)

( * ) Notice: Subject to any disclaimer, the term of this patent is extended or adjusted under 35 U.S.C. 154(b) by 0 days.

(21) Appl. No.: 09/490,109

(22) Filed: Jan. 24, 2000

Related U.S. Application Data

(62) Division of application No. 09/180,372, filed as application No. PCT/AU97/00452 on Jul. 18, 1997, now Pat. No. 6,207,402.

(30) Foreign Application Priority Data

Jul. 18, 1996 (AU) ............................................. PO 1113
Oct. 30, 1996 (AU) ............................................. PO 3323

(51) Int. Cl.$^7$ ................................................. C12N 9/42

(52) U.S. Cl. ......................... 435/209; 435/814; 435/815
(58) Field of Search ................................. 435/209, 814, 435/815

(56) References Cited

U.S. PATENT DOCUMENTS

| | | | |
|---|---|---|---|
| 4,859,581 A | * | 8/1989 | Nicolson et al. |
| 5,206,223 A | | 4/1993 | Vlodovsky et al. |
| 5,262,403 A | * | 11/1993 | Nicolson et al. |
| 5,362,641 A | * | 11/1994 | Fuks et al. |
| 5,739,115 A | | 4/1998 | Fugedi et al. |

FOREIGN PATENT DOCUMENTS

| | | | |
|---|---|---|---|
| WO | | 91/19197 | 12/1991 |
| WO | WO-9504158 A | * | 2/1995 |

OTHER PUBLICATIONS

Graham et al., "Comparison of the Heparanase Enzymes from Mouse Melanoma Cells, Mouse Macrophages, and Human Platelets" (1996) Biochem. Mol. Biol. Internat., 39(3), 563–571.*
Nakajima et al., "Heparanases and Tumor Metastasis" (1988) J. Cell. Biochem., 36(2), 157–167.*
Hoogewerf et al., "Isolation of Human Platelet Heparanase: Identity with Connective Tissue Activating Peptide (CTAP–III)" (1993) Mol. Biol. Cell, 4, 268a, Abstract 1657.*
Yahalom et al., "Degradation of Sulfated Proteoglycans in the Subendothelial Extracellular Matrix by Human Platelet Heparatinase" (1984) J. Clin. Invest., 74(5), 1842–1849.*
Hoogewerf et al., "CXC Chemokines Connective Tissue Activating Peptide–III and Neutrophil Activating Peptide–2 are Heparin/Heparan Sulfate–Degrading Enzymes" (1995) J. Biol. Chem., 270(7), 3268–3277.*

Kosir et al., "Early Human Breast Carcinoma Cells Produce Extracellular Heparanase" (1996) Proc. Amer. Assoc. Canc. Res. (87th Annual Meeting), 37, 495, Abst# 3378.*
Bar–Ner et al. "Sequential Degradation of Heparan Sulfate in the Subendothelial Extracellular Matrix by Highly Metastatic Lymphoma Cells." Int. J. Cancer 35:483–491 (1985).
Bartlett, et al. "Comparative analysis of the ability of leucocytes, endothelial cells and platelets to degrade the subendothelial basement membrane: Evidence for cytokine dependence and detection of a novel sulfatase." Immunol. Cell Biol. 73:113–124 (1995).
Brown, et al. "Histidine–Rich Glycoprotein and Platelet Factor 4 Mask Heparan Sulfate Proteoglycans Recognized by Acidic and Basic Fibroblast Growth Factor." Biochemistry. 33(46):13918–13927 (1994).
Castellot Jr. et al. "Inhibition of Vascular Smooth Muscle Cell Growth by Endothelial Cell–derived Heparin." J. Biol. Chem. 257:11256–11260 (1982).
Eldor et al. "Role of Heparanase in Platelet and Tumor Cell Interactions with the Subendothelial Extracellular Matrix." Sem. Thromb. Haem. 13:475–488 (1987).
Freeman, et al. "A Rapid Quantitative Assay for the Detection of Mammalian Heparanase Activity." Biochem. J. 325: 229–237 (1997).
Gallagher et al. "Heparan sulphate–degrading endoglycosidase in liver plasma membranes." Biochem J. 250:719–726 (1988).
Gilat et al. "Molecular behaviour adapts to context: Heparanase functions as an extracellular matrix–degrading enzyme or as a T cell adhesion molecule, depending on the local pH." J. of Experimental Medicine. 181:1929–1934 (1995).
Graham, et a. "Comparison of the heparanse enzymes from mouse melanoma cells, mouse macrophages and human platelets." Biochemistry and Molecular Biology International. 39:563–571 (1996).
Hennes, et al. "Matrix heparan sulphate, but not endothelial cell surface heparan sulphate, is degraded by highly metastatic mouse lymphoma cells." Br. J. Cancer. 58:186–188 (1988).
Heldin, et al. "Characterization of Platelet Endoglycosidase Degrading Heparin–like Saccharides." Biochemistry. 19:5755–5762 (1980).
Höök, et al. "A Heparan Sulfate–degrading Endoglycosidase From Rat Liver Tissue." Biochem. and Biophys. Res. Comm. 67:1422–1428 (1975).

(List continued on next page.)

Primary Examiner—Jon P. Weber
(74) Attorney, Agent, or Firm—Burns, Doane, Swecker & Mathis, LLP

(57) ABSTRACT

A method for the purification of human platelet heparanase using chromatographic techniques is described. The method comprises detergent-aided solubilization of a heparanase-containing fraction followed by purification of the heparanase therefrom by concanavalin A, $Zn^{2+}$-chelating Sepharose, a Blue A or Reactive Red matrix, octyl agarose and gel filtration chromatography. Heparanase so purified has a molecular mass (Mr) of about 50 kDa and degrades both heparin and heparan sulfates.

6 Claims, 8 Drawing Sheets

OTHER PUBLICATIONS

Figure 1:
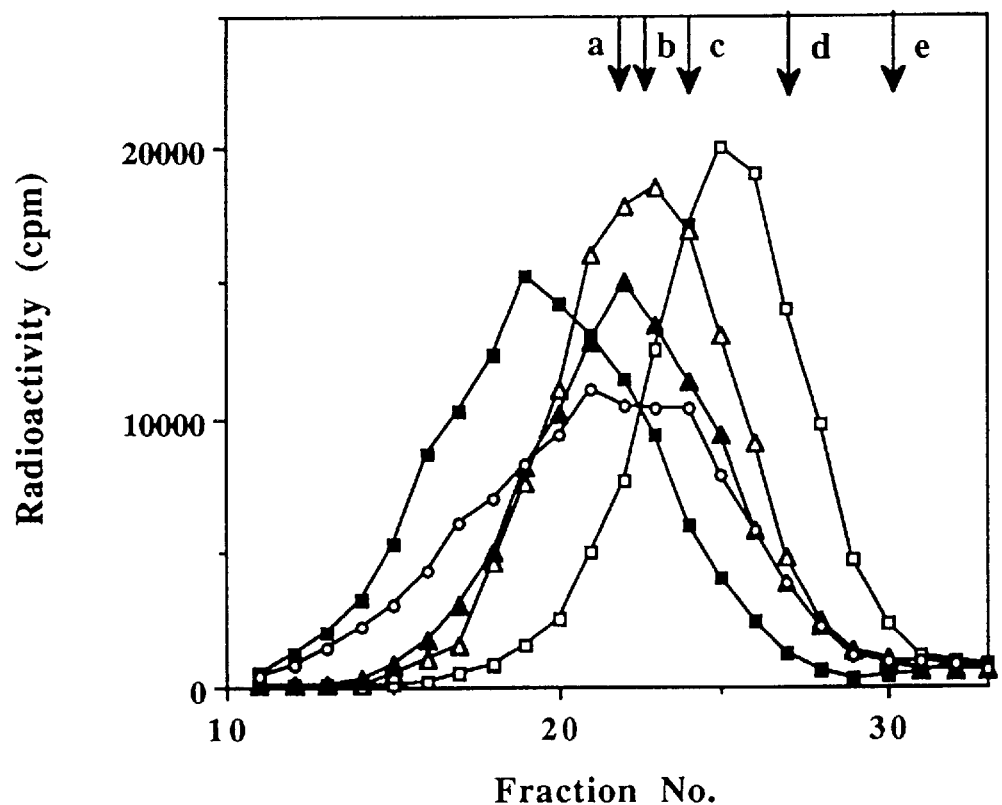

Irimura et al. "Chemically Modified Heparins as Inhibitors of Heparan Sulfate Specific Endo–β–glucuronidase (Heparanase) of Metastatic Melonoma Cells." *Biochemistry.* 25:5322–5328 (1986).

Jin et al. "Immunochemical Localization of Heparanase in Mouse and Human Melanomas." *Int. J. Cancer.* 45:1088–1095 (1990).

Klein, et al. "Partial Purifacation and Characterization of a Heparan Sulfate Specific Endoglucuronidase." *Biochem. Biophys. Res. Commun.* 73:569–576 (1976).

Laskov, et al. "Production of Heparanase by Normal and Neoplastic Murine B–Lymphocytes." *Int. J. Cancer.* 47:92–98 (1991).

Lider, et al. "Suppression of Experimental Autoimmune Diseases and Prolongation of Allograft Survival by Treatment of Animals with Low Doses of Heparins." *J. Clin. Invest.* 83:752–756 (1989).

Matzner, et al. "Degradation of Heparan Sulfate in the Subendothelial Extracellular Matrix by a Readily Released Heparanase from Human Neutrophils." *J. Clin, Invest.* 76:1306–1313 (1985).

Matzner, et al. "Subcellular localization of heparanase in human neutrophils." *J. Leukoc. Biol.* 51:519–524 (1992).

Nakajima, et al. "Haparan Sulfate Degradation: Relation to Tumor Invasive and Metastatic Properties of Mouse B16 Melanoma Sublines." *Science.* 220:611–613 (1983).

Naparstek, et al. "Activated T lymphocytes produce a matrix–degrading haparan sulphate endoglycosidase." *Nature.* 310:241–244 (1984).

Oosta, et al. "Purification and Properties of Human Platelet Heparitinase." *J. Biol. Chem.* 257:11249–11255 (1982).

Parish, et al. "A Basement–Membrane permeability assay which correlates with the metastatic potential of tumour cells." *Int. J. Cancer.* 52:378–383 (1992).

Ricoveri, et al. "Heparan Sulfate Endoglycosidase and Metastatic Potential in Murine Fibrosarcoma and Melanoma." *Cancer Res.* 46:3855–3861 (1986).

Rylatt, et al. "Autorosette Inhibition Factor: isolation and Properties of the Human Plasma Protein." *Eur. J. Biochem.* 119: 641–46 (1981).

Sewell, et al. "Human mononuclear cells contain an endoglycosidase specific for heparan sulphate glycosaminoglycan demonstrable with the use of a specific solid –phase metabolically radiolabelledsubstrate." *Biochem J.* 264:777–783 (1989).

Thunberg, et al. "Enzymatic Depolymerization of Heparin –related Polysaccharides." *J. Biol. Chem.* 257:10278–10282 (1982).

Vlodavsky, et al. "Expression of Heparanase by Platelets and Circulating Cells of the Immune System: Possible Involvement in Diapedesis and Extravasation." *Invasion Metastasis.* 12:112–127 (1992).

Wasteson, et al. "Demonstration of a Platelet Enzyme, Degrading Heparan Sulphate." *FEBS Letters.* 64:218–221 (1976).

\* cited by examiner

METHOD FOR THE PURIFICATION OF HUMAN PLATELET HEPARANASE

This application is a divisional of application Ser. No. 09/180,372, filed Dec. 28, 1998, now U.S. Pat. No. 6,209,402 which is the National Stage pursuant to 35 U.S.C. 371 of International Patent Application Ser. No. PCT/AU97/00452 filed Jul. 18, 1997.

FIELD OF INVENTION

This invention relates to an assay for the detection of mammalian heparanase activity present in a variety of mammalian tissues, cells and bodily fluids, including serum and both normal and cancerous cells and tissues, and which may be used for the determination of mammalian heparanase activity from a variety of tissue and cell sources, as a diagnostic tool for the determination of metastatic potential, and for the development of specific inhibitors of heparanase activity and metastasis.

The invention also relates to a method for the purification of mammalian heparanase, in particular human platelet heparanase, and to the purified mammalian heparanase obtainable by this method. The availability of purified mammalian heparanase such as human platelet heparanase will facilitate the development of inhibitors of mammalian heparanase activity, the production of monoclonal antibodies against the enzyme, and the identification of amino acid and cDNA sequence of the enzyme for the ultimate cloning and the expression of the enzyme.

BACKGROUND OF THE INVENTION

Important processes in tissue invasion by blood-borne malignant tumour cells and leukocytes include their adhesion to the luminal surface of the vascular endothelium, their passage through the vascular endothelial cell layer and the subsequent degradation of the underlying basal lamina and extracellular matrix (ECM) with a battery of secreted and/or cell surface protease and glycosidase activities (Nakajima et al, 1983; Schmitt et al, 1992; Vlodavsky et al, 1992). The basal lamina and underlying connective tissue stroma consist predominantly of a complex network of fibronectin, laminin, collagen type IV and vitronectin, each of which interact with heparan sulphate (HS) side chains of heparan sulphate proteoglycans (HSPG) embedded within the matrix (Yurichenco and Schittny, 1990). HS chains generally consist of clusters of sulphated disaccharide units (predominately N-sulphated glucosamine linked 1→4 to α-L-iduronic acid residues) separated by lowly or non-sulphated regions (predominately disaccharide units of N-acetylated glucosamine linked 1→4 to β-D-glucuronic acid) (Turnbull and Gallagher, 1990,1991). Cleavage of the HS chains by endoglycosidase or heparanase activity produced by invading cells may therefore assist in the disassembly of the ECM and facilitate cell migration. Heparanase activity has been shown to be related to the metastatic potential of murine and human fibrosarcoma and melanoma cell lines (Nakajima et al, 1983, 1986a,b, 1988; Ricoveri and Cappelletti, 1986). Furthermore, heparanase activity has been described in a number of tissues and cell types including rat liver (Gallagher et al, 1988; Hook et al, 1975), human placenta (Klein and Von Figura, 1979; Lider et al, 1989), human platelets (Hoogewerf et al, 1995; Oldberg et al, 1980; Oosta et al, 1982), cultured human skin fibroblasts (Klein and Von Figura, 1976), human neutrophils (Matzner et al, 1985, 1992), activated but not resting rat T-lymphocytes (Naparstek et al, 1984), normal and neoplastic murine B-lymphocytes (Laskov et al, 1991), human monocytes (Sewell et al, 1989) and human umbilical vein endothelial cells (Bartlett et al, 1995; Godder et al, 1991). Because the cleavage of HS appears to be essential for the passage of metastatic tumour cells and leukocytes through basement membranes, studies of heparanase inhibitors provide the potential of developing novel and highly selective classes of anti-metastatic and anti-inflammatory drugs (Coombe et al, 1987; Irimura et al, 1986; Parish et al, 1990; Vlodavsky et al, 1992; Willenborg and Parish 1988).

The expression of heparanase activity by platelets, metastatic tumour cells and circulating cells of the immune system has been related to their involvement in their diapedes and extravasation. Studies have shown that while the initial entrapment of metastatic tumour cells by the capillary endothelium is platelet-independent, platelet aggregation which occurs shortly afterwards can lead to platelet activation and degranulation, resulting in gap formation and retraction of endothelial cells exposing the underlying basement membrane to adhesion by the tumour cells (Tanaka et al, 1986; Crissman et al, 1985; Yahalom et al, 1985). Human platelets have been shown to contain high levels of heparanase activity, capable of degrading endothelial cell surface, tumour-derived and ECM-derived HSPG (Bartlett et al, 1995a, 1995b; Castellot et al, 1982; Hoogewerf et al, 1995; Wasteson et al, 1976, 1977; Yahalom et al, 1984; ) as well as free HS and heparin chains (Graham et al, 1995a and b; Oldberg et al, 1980; Oosta et al, 1982; Wasteson et al, 1976, 1977). To date, three separate mammalian cell heparanase activities have been reported: mouse melanoma B16 heparanase which cleaves HS only, human platelet heparanase which cleaves both heparin and HS and a mouse mastocytoma endoglucuronidase which was reported to cleave newly synthesised heparin precursor but not heparin or HS (Hoogewerf et al 1995; Nakajima et al, 1988; Thunberg et al, 1982). More recent studies have indicated that murine melanoma and macrophage extracts are in fact able to degrade both HS and heparin, however heparin was degraded to a lesser extent than by human platelet extracts (Graham and Underwood, 1996). Although Hennes et al (1988) reported that tumour-derived heparanase was able to degrade matrix HS but was unable to degrade endothelial cell surface HS, human platelets have been shown to degrade endothelial cell surface HS (Wasteson et al, 1977) which was shown by Gamse et al (1978) to be more heparin-like in structure. Thus, it is likely that the platelet heparanase, which is capable of degrading both heparin and HS, may play a critical role in degrading cell-surface HS in focal adhesion plaques, and aiding the extravasation of blood-borne cells.

Following partial purification of human platelet heparanase by Oldberg et al (1980), who determined that the enzyme was an endoglucuronidase which acted upon N-sulphated, iduronic acid-containing heparin biosynthetic intermediates, the enzyme was purified 240,000-fold to apparent homogeneity in 6% yield by a 6-column procedure (Oosta et al, 1982). The enzyme was a 134 kDa single subunit protein which was active towards $^{125}$I-heparin and was confirmed to be an endoglucuronidase. In subsequent studies, the platelet heparanase was shown to cleave endothelial cell surface heparin-like material which inhibited smooth muscle cell proliferation (Castellot et al, 1982) and to cleave the antithrombin III (AT III)-binding octasaccharide between GlcA-GlcNS3S (Thunberg et al, 1982), presumably resulting in the loss of the anticoagulant activity of heparin following its degradation (Oldberg et al, 1980). Although, the purified enzyme was shown to act towards an octasaccharide substrate, platelet extracts were also shown to degrade ECM-derived HS chains to 10 kDa (Yahalom, et al 1984) and to 5 kDa fragments (Freeman and Bartlett, unpublished observations), indicating the existence of specific structural motifs determining the site of cleavage. The size of heparin-cleavage products following platelet heparanase action has not been determined (Graham and Underwood, 1996; Oldberg et al, 1980; Oosta et al, 1982). Recently, however, Hoogewerf et al (1995) reported the 4100-fold purification of a human platelet heparanase activity in 8% yield which was shown to be an endoglucosaminidase that cleaved both heparin and HS principally to disaccharides following radiolabelling of the digestion products. The activity resided in the 8–10 kDa subunit CXC chemokines connective tissue activating peptide-III (CTAP-III) and neutrophil activating peptide-2 (NAP-2) which are members of the platelet basic protein family. In contrast, Graham and Underwood (1996) has since shown that the heparanase activity in human platelet extracts had a Mr of 40–60 kDa, and cleaved both HS and heparin, although the size of the degradation products was not determined.

The resolution of the reported differences in the molecular size (8 to 134 kDa), the substrate specificity (whether the enzyme is an endo-glucuronidase or endo-glucosaminidase activity), and the size of the substrate cleavage products (disaccharides or 5 to 10 kDa) requires purification of the enzyme(s) to homogeneity in high yield. While some studies of the substrate specificity of the platelet enzyme have been reported (Oldberg, et al 1980; Oosta et al, 1882; Thunberg, et al 1982), surprisingly little has been reported on the inhibition of the enzyme by sulphated polysaccharides (similar to the studies by Nakajima et al (1986a and b)) on the inhibition of tumour cell heparanase activity) apart from the use of some modified heparins and heparin itself to inhibit platelet degradation of ECM-associated HSPG (Eldor, et al 1987). This is especially surprising considering the potentially important role of platelets during the initial stages of tumour cell extravasation.

In order to purify and characterise mammalian heparanase activities and to screen for and develop effective heparanase inhibitors, a simple and rapid assay for heparanase activity is required. However, previous heparanase assays have been cumbersome and time consuming in both preparation of radiolabelled substrate and separation of degradative products from the uncleaved substrate. Frequently heparanase assays have involved the biosynthetic radio-labelling of ECM-associated HSPG and the detection of HS chain degradation by gel filtration analysis of radiolabelled material released from the ECM (Bartlett et al, 1995; Vlodavsky et al, 1992 and references within). Such an approach suffers from the main disadvantage that degradation of HS chains in an ECM involves the synergistic action of proteases which are required to expose the HS chains for subsequent heparanase attack (Bar-Ner et al, 1985, 1986; Benezra et al, 1992; Vlodavsky et al, 1988). Furthermore, most heparanase assays have required extensive degradation of the radiolabelled HS (or ECM-derived HSPG) substrate to allow separation of the degraded product from the substrate by gel filtration (Bartlett et al, 1995; Klein and Von Figura, 1979; Nakajima et al, 1986a; Vlodavsky et al, 1992), although cleavage of HS chains at a single site may be all that is required to allow passage of leukocytes and tumour cells through the basement membrane. Solid phase heparanase assays also have been developed where chemically and biosynthetically radiolabelled heparin and HS chains were attached to a solid support with release of radiolabel from the solid support being a measure of enzyme activity (Nakajima et al, 1986a; Oosta et al, 1982; Sewell et al, 1989). Such assays, however, suffer from the disadvantage that the immobilized substrate may be less accessible to the mammalian heparanase enzyme, and the coupling of the radiolabelled substrate to the solid support, via the substrate's reducing terminus, is a complex and inefficient procedure. Previous studies have also radiolabelled both heparin and HS by iodination at naturally occurring glucosamine residues (Oosta et al, 1982) or by N-acetylation of the partially de-N-sulphated substrate (Nakajima et al, 1986a). Such procedures, however, may result in the masking, or the creation of new heparanase cleavage sites.

SUMMARY OF THE INVENTION

In one aspect, the present invention provides a method for detecting mammalian heparanase activity in a sample such as mammalian tissue, cells or bodily fluids.

In accordance with this aspect, the present invention provides a method for the detection of mammalian heparanase activity in a sample, which comprises the steps of:
(i) contacting the sample to be tested with a heparanase substrate for a time and under conditions sufficient for heparanase in the sample to degrade the heparanase substrate;
(ii) separating degradation products from undegraded or partially degraded heparanase substrate by binding the undegraded or partially degraded heparanase substrate with a heparan sulphate-binding protein; and
(iii) detecting separated degradation products to indicate heparanase activity in the sample.

In this aspect, the present invention also provides a kit for use in the detection of mammalian heparanase activity in a sample, which comprises, in compartmentalized form:
(i) heparanase substrate;
(ii) heparan sulphate-binding protein; and
(iii) optionally, directions for performing the method of the invention as broadly described above.

In another aspect, the present invention provides a novel procedure for the rapid purification of mammalian heparanase activity, more particularly human platelet heparanase activity, as well as purified mammalian heparanase prepared by this procedure.

According to this aspect, the present invention provides a method for the purification of mammalian heparanase from a heparanase-containing material, which comprises the steps of:
(i) contacting the heparanase-containing material with an immobilised lectin affinity chromatography matrix in the presence of detergent to bind heparanase activity to said matrix;
(ii) eluting a first purified heparanase-containing fraction from said matrix;
(iii) optionally contacting said first purified heparanase-containing fraction with an immobilised metal ion affinity chromatography matrix;
(iv) contacting said first purified heparanase-containing fraction with a dye-resin matrix to bind heparanase activity to said dye-resin matrix; and
(v) eluting a second purified heparanase-containing fraction from said dye-resin matrix.

In this aspect, the present invention also provides substantially purified mammalian heparanase prepared by the method described broadly above, in particular substantially purified human platelet heparanase characterised in that it has a native molecular mass (Mr) of about 50 kDa when analysed by gel filtration chromatography and by SDS-PAGE, and in that it degrades both heparin and heparan sulphate. The substantially purified human platelet heparanase of this invention degrades bovine lung and porcine mucosal heparin from 12 kDa to 6 and 4 kDa fragments respectively, and porcine mucosal heparan sulphate in a stepwise fashion from 22 kDa to 5 kDa fragments, by gel filtration analysis.

The heparanase purification method of this invention as broadly described above may also be used to purify other heparanases, including rat liver, rat 13762 MAT adenocarcinoma cell and human HCT116 colonic carcinoma cell heparanase. Substantially purified MAT and HCT cell heparanase have similar Mr to the human platelet heparanase discussed above, while substantially purified rat liver heparanase has a native Mr of about 45 kDa and has 3 bands on SDS-PAGE between 43 and 47 kDa.

Throughout this specification, unless the context requires otherwise, the word "comprise", or variations such as "comprises" or "comprising", will be understood to imply the inclusion of a stated integer or group of integers but not the exclusion of any other integer or group of integers.

DETAILED DESCRIPTION OF THE INVENTION

In one aspect, the present invention relates in particular to the detection of mammalian heparanase activity in serum, including serum of human cancer patients, as well as in a variety of tissue and cell homogenates or extracts, including for example human platelets, colonic carcinoma cells, umbilical vein endothelial cells and rat mammary adenocarcinoma cells (both metastatic and non-metastatic variants) and liver homogenates. The method may be used to determine heparanase activity in both human and non-human (e.g. rat and murine) sera, cell and tissue homogenates or extracts.

Preferably, the heparanase substrate is a labelled substrate, more preferably a radiolabelled substrate. The substrate is preferably heparan sulphate (HS) and particularly preferred substrates are $^3$H-porcine mucosal HS and $^3$H-bovine kidney HS. Preferably, porcine mucosal HS is partially de-N-acetylated and re-N-acetylated with $^3$H-acetic anhydride to yield the desired radiolabelled substrate.

As broadly described above, the sample to be tested is contacted with the heparanase substrate for a time and under conditions sufficient for heparanase, if any, in the sample to degrade the substrate. Suitable incubation times and conditions can be readily determined without undue experimentation. By way of example, incubation of the sample with the substrate may be carried out at a temperature in the range of 35° C. to 40° C., preferably about 37° C., for a period of from 2 to 48 hrs, preferably about 16 hrs, at a pH in the range of from 4.2 to 7.5, preferably about pH 5.1. Preferably, the incubation step is performed in the presence of bovine serum albumin, N-acetylmannosamine and/or a detergent such as Triton X-100. As described in detail below, heparanase activity under suitable incubation times and conditions degrades the preferred porcine mucosal heparan sulphate substrate in a stepwise fashion from 22 to 17, then to 8 and finally to 5 kDa fragments or degradation products.

Separation of degradation products from undegraded or partially degraded heparanase substrate is carried out by binding to a heparan sulphate-binding protein. As used herein, the term "heparan sulphate-binding protein" includes, but is not limited to heparin-binding proteins. A particularly preferred heparan sulphate-binding protein for use in the present invention is histidine-rich glycoprotein. More preferably, the histidine-rich glycoprotein (HRG) is chicken HRG, however other HRG including human HRG may also be used. It is to be understood, however, that the present invention extends to the use of other heparan sulphate- and heparin-binding proteins other than HRG including, for example, protease inhibitors such as antithrombin 111 and heparin cofactor 11; plasma lipoproteins such as apolipoprotein B-100 and apolipoprotein E; growth factors such as acidic and basic fibroblast growth factor, vascular endothelial growth factor, hepatocyte growth factor and platelet-derived growth factor; extracellular matrix proteins such as laminin, collagen and elastin; enzymes such as lipoprotein lyase, superoxide dimutase, cathepsin G, elastase and the bacterial heparin lyases 1, 11 and 111; and other suitable binding proteins such as platelet factor 4, von willebrand factor, and β-thromboglobulin. The present invention also extends to peptides derived from these heparan sulphate- or heparin-binding proteins particularly HRG, which contain the heparan sulphate- or haparin-binding region.

Preferably, the separation is carried out by binding to an immobilised heparan sulphate-binding protein. Any suitable method of immobilisation may be used, however it is presently preferred to immobilise HRG or other suitable binding protein by binding to agarose, more particularly Sepharose, beads. in this preferred aspect, the HRG-Sepharose beads may be loaded in a column, and the incubation mixture applied to and washed through the column to bind undegraded or partially degraded heparanase substrate, with degradation products being unbound or bound less efficiently to the HRG-Sepharose beads. Alternatively, the HRG or other suitable binding protein may be added to an incubation mixture to bind to undegraded or partially degraded heparanase substrate complex, and the complex may then be separated, for example by immobilisation on a substrate (such as Immobilon or StrataClean) leaving degraded heparanase substrate fragments in the incubation mixture following removal of the immobilised complex, for example by centrifugation or filtration.

In the final step of the method of this aspect of the invention, separated degradation products are detected to indicate the presence of heparanase activity in the sample under test. This detection step may include quantitative and/or qualitative detection of the degradation products. Where a radiolabelled heparanase substrate such as a $^3$H-porcine mucosal HS is used, the detection step may consist of detection of radioactivity levels of unbound degradation products.

The present invention provides in this aspect a novel method for separating degradation products from the heparanase substrate by taking advantage of the decreased affinity of the cleaved heparanase degradation products for a heparan sulphate-binding protein such as HRG, particularly chicken histidine-rich glycoprotein (cHRG). Incubation mixtures are applied to cHRG-Sepharose columns, with unbound material corresponding to heparanase degradation products. Heparanase activity has been determined for a variety of human, rat and murine cell and tissue homogenates. By way of example, highly metastatic rat mammary adenocarcinoma and murine melanoma cell lines had 4 to 10 times the heparanase activity compared to non-metastatic variants, confirming the correlation of heparanase activity with metastatic potential. Human cancer patients had twice the serum heparanase levels as normal healthy adults.

This aspect of the present invention provides a new, simple and rapid quantitative assay for the detection of mammalian heparanase activity towards a natural radiolabelled substrate which can detect the minimal number of HS chain cleavages which are likely to occur in vivo, and which is based upon a novel principle, namely the loss of a protein binding site on HS chains following chain cleavage. In the assay, advantage is taken of an initial observation that the HS-binding plasma protein HRG masks heparanase cleavage sites on HS chains. Following heparanase digestion, radiolabelled HS fragments (products) are not bound by mini-columns of HRG-coupled Sepharose beads unlike the remaining intact and partially degraded substrate, allowing a rapid separation of the cleaved product from the substrate.

The assay of this aspect of the invention has several advantages over conventional assays in (a) ease of preparation of relatively large quantities of a radiolabelled natural substrate while maintaining the native structure, (b) allowing the rapid and simultaneous determination of a large number of samples and (c) allowing accurate quantification of heparanase activity by detecting single site cleavage of the substrate.

In another aspect, the present invention relates to the purification of mammalian heparanase from heparanase-containing material. The heparanase-containing material which is used as a starting material in the method of the present invention may be any source of mammalian heparanase activity, for example human colonic carcinoma HCT 116 cells, rat mammary adenocarcinoma 13762 MAT cells, or rat liver tissue. The present invention is, however, particularly directed to purification of human platelet heparanase, and a convenient source of this material is obtained by solubilisation of enzyme activity from a homogenate of frozen, washed human platelets.

The heparanase-containing material is subjected to immobilised lectin affinity chromatography, preferably concanavalin A-Sepharose chromatography, in the presence of detergent (such as Triton X-100) to bind the heparanase activity to the chromatography column. Elution of the bound heparanase activity provides a first purified heparanase-containing fraction.

Optionally, and preferably, the first purified heparanase-containing fraction is then subjected to immobilised metal ion affinity chromatography (IMAC), preferably using a matrix such as $Zn^{2+}$-chelating Sepharose, which does not bind the hep-aranase activity but which removes other contaminating proteins. The first purified heparanase-containing fraction is then subjected to dye-resin chromatography, preferably in series with the IMAC matrix, to again bind the heparanase activity. Suitable dye-resin matrixes include a Blue-A agarose matrix, although other dyes such as Reactive Red may also be used as well as other matrix supports such as Sepharose and acrylamide. Elution of a second purified heparanase-containing fraction from the dye-resin matrix may be followed by octyl-agarose chromatography which again binds contaminating proteins without binding the heparanase activity.

Final purification of the second purified heparanase-containing fraction may be carried out by gel filtration chromatography, for example Superose 12 chromatography, optionally followed by concentration of the purified enzyme.

As previously described the product obtained in accordance with this aspect of the present invention is substantially purified mammalian heparanase, in particular substantially purified human platelet heparanase. The term "substantially purified" as used in the present specification denotes that the product has been subjected to purification procedures such that the heparanase enzyme activity is at least 1000-fold, preferably at least 1,500-fold when compared with the activity of the heparanase-containing starting material.

Preferably also, the substantially purified mammalian heparanase is homogeneous, and preferably contains at least 75% by weight, even more preferably at least 85% by weight, and most preferably at least 95–99% by weight of the heparanase enzyme, relative to other proteins with which it is normally associated in its native form.

In accordance with this aspect of the present invention, human platelet heparanase has been purified to homogeneity from previously frozen, washed platelets. Human platelets have been shown to contain very high amounts of heparanase activity compared to metastatic tumour cells and other cell types when expressed as activity/mg of protein.

In one embodiment of this aspect of the method of this invention which is described in detail in the Example below, human platelet heparanase has been purified 1900-fold to homogeneity in 19% yield by a five column procedure, which consists of concanavalin A-Sepharose, $Zn^{2+}$-chelating-Sepharose, Blue A-agarose, octyl-agarose and gel filtration chromatography. The same purification procedure can be used to purify other mammalian heparanase activities, eg from human colonic carcinoma HCT 116 cells, rat mammary adenocarcinoma 13762 MAT cells and from rat liver. The human platelet heparanase, which degrades both heparin and HS, had a native molecular mass of 50 kDa when analysed by gel filtration chromatography and by SDS-PAGE. The enzyme degraded porcine mucosal HS in a stepwise fashion from 22 to 17, 10 and finally to 5 kDa fragments while bovine lung and porcine mucosal heparin were degraded from 12 kDa to 6 and 4 kDa fragments respectively by gel filtration analysis.

Further details of the present invention will be apparent from the detailed description in the following Example which is included by way of illustration and not limitation of the invention, and the accompanying drawings.

In the drawings:

FIG. 1: Degradation of HS as a function of incubation pH. HS was incubated with rat 13762 MAT homogenate at pH 4.2 (○), 5.1 (□), 6.5 (Δ) and 7.5 (▲) and in the absence of added enzyme at pH 5.1 (■) for 16 h at 37° C. The incubation mixtures were fractionated by Superose-6 gel filtration chromatography. Mr standards shown are a) 16.7, b) 10.6. c) 6.7, d) 3.1 and e) 0.2 kDa. For full details, see the Methods section.

Figure 2:
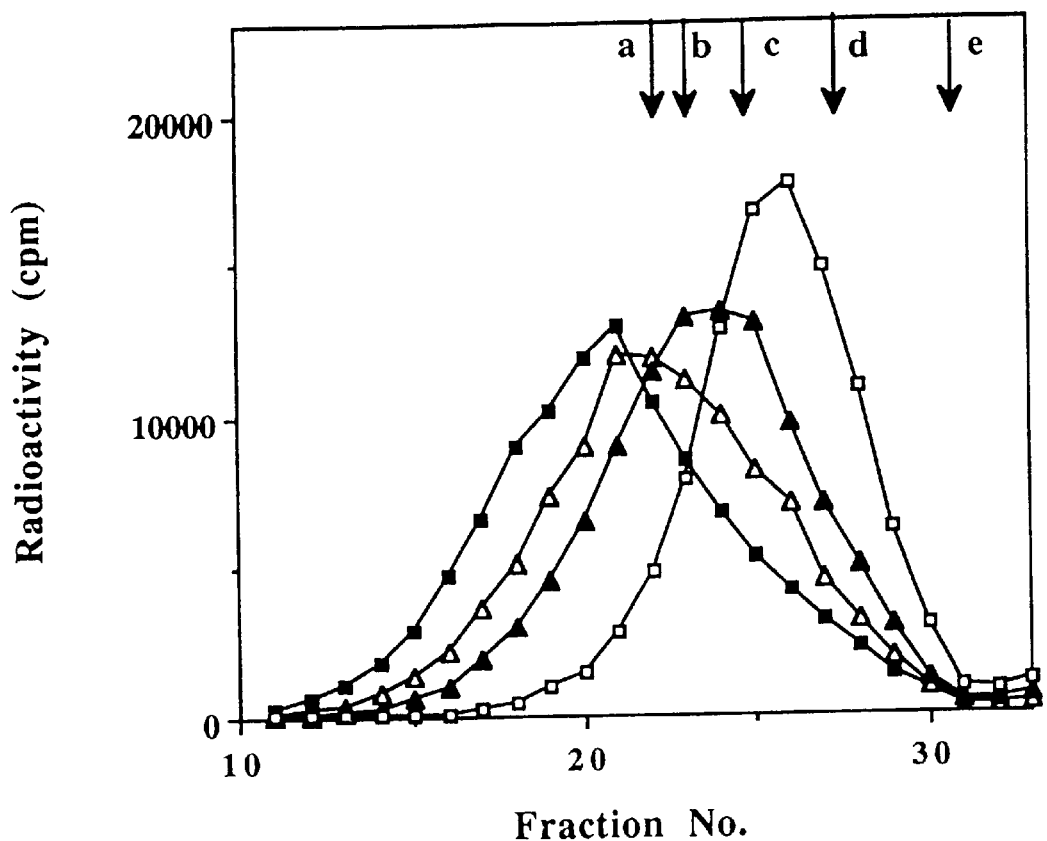

FIG. 2: Degradation of HS as a function of incubation time. HS was incubated with rat 13762 MAT homogenate at pH 5.1 for 2 (Δ), 4 (▲) and 16 hr (□) and in the absence of added enzyme for 4 hr (■) at 37° C. The incubation mixtures were fractionated by Superose 6 gel filtration chromatography. Mr standards a–e are as described in FIG. 1. For full details, see the Methods section.

Figure 3:
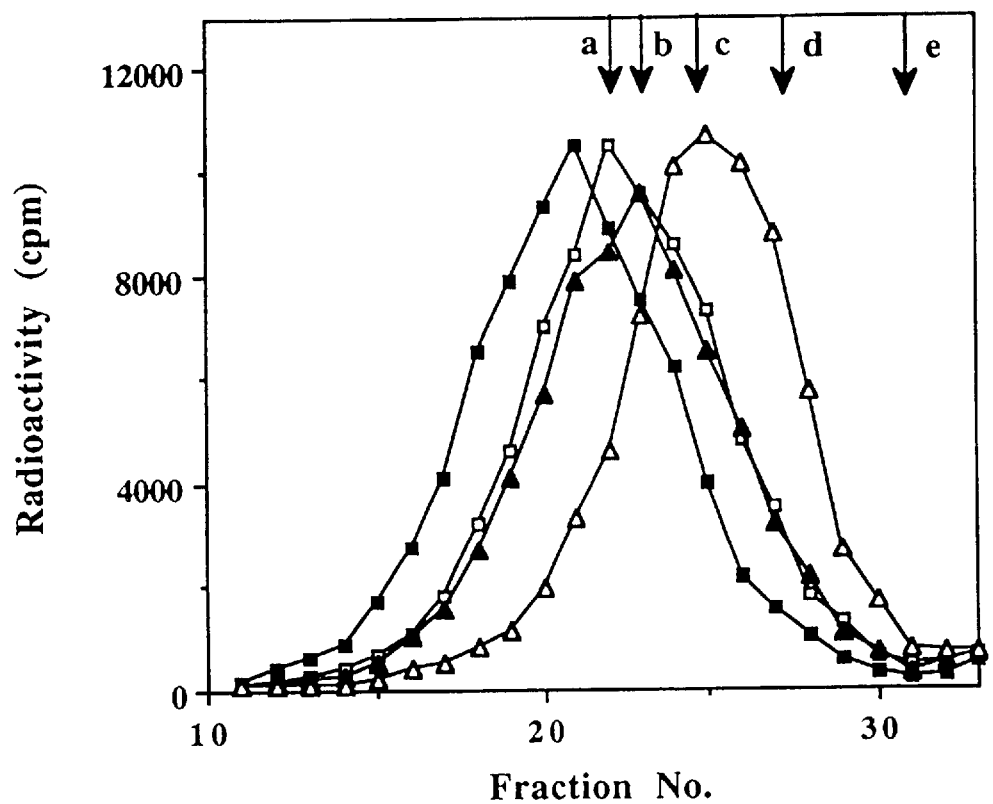

FIG. 3: Degradation of HS by homogenates of metastatic and non-metastatic rat mammary adenocarcinoma cell lines. HS was incubated at pH 5.1 for 16 h at 37° C. with no enzyme (■), homogenates of the non-metastatic variants DMBA-Sask (□) and 13762 MAT (J-clone) (▲) and the highly metastatic 13762 MAT and DMBA-8A cell lines (Δ) shown together for convenience. The incubation mixtures were fractionated by Superose 6 gel filtration chromatography. Mr standards a–e are as described in FIG. 1. For full details, see the Methods section.

Figure 4:
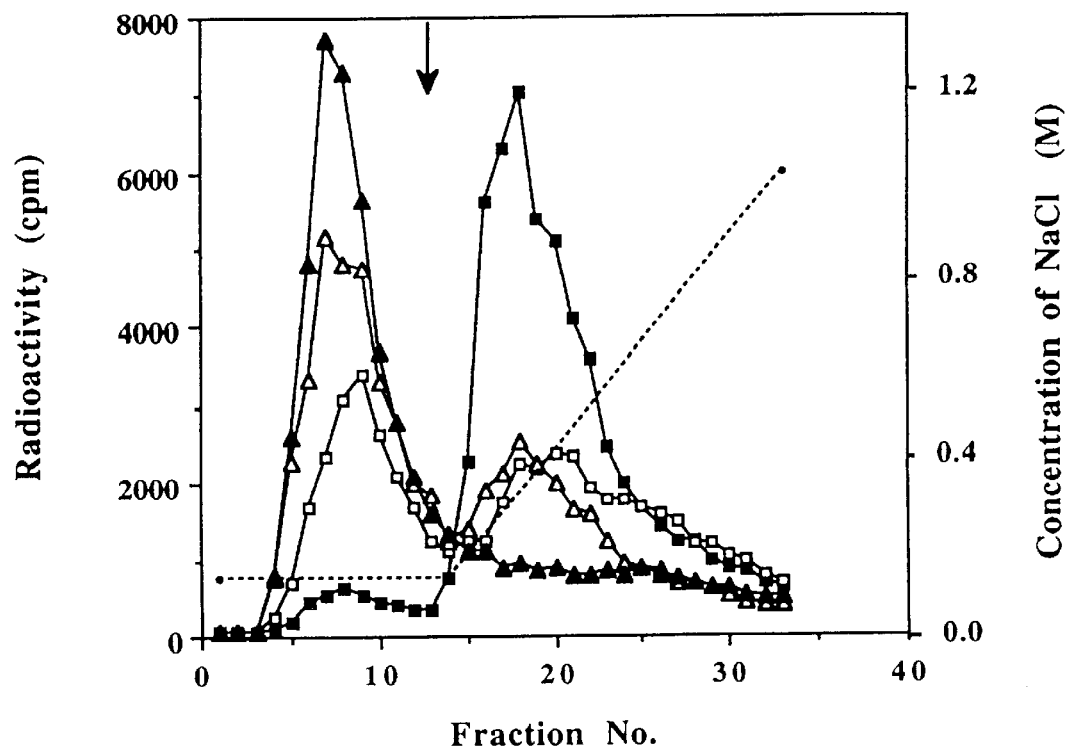

FIG. 4: Degradation of HS as a function of incubation time and affinity of the digested HS products for cHRG-Sepharose. HS was incubated at pH 5.1 for 2 (□), 4 (Δ) and 16 hr (▲) and in the absence of added enzyme for 4 hr (■) at 37° C. The incubation mixtures were applied to a cHRG-Sepharose column in PBS, washed with PBS and eluted by a NaCl-gradient. The arrow indicates the start of the NaCl gradient.—, Concentration of NaCl. For full details, see the Methods section.

Figure 5:
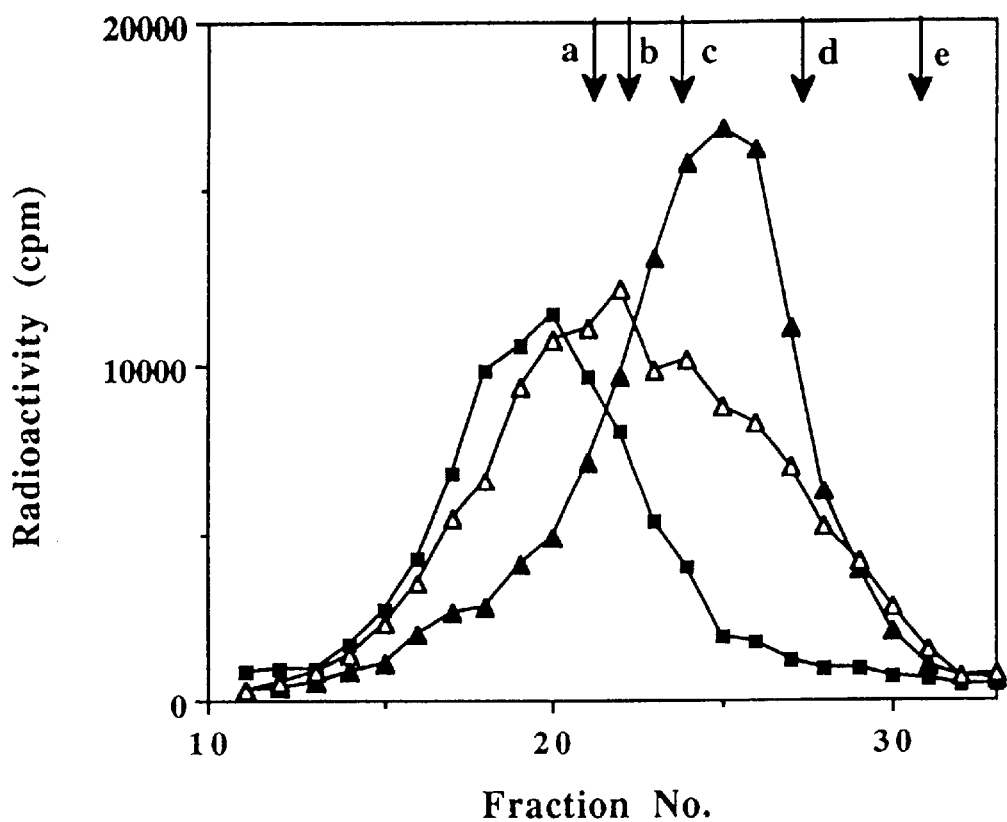

FIG. 5: Inhibition of HS degradation by cHRG. HS was incubated at pH 5.1 for 8 h at 37° C. in the absence of added enzyme or cHRG (■) and with rat 13762 MAT cell homogenate in the presence (Δ) and absence (▲) of a 3:1 (cHRG:HS) molar ratio of cHRG. The incubation mixtures were fractionated by Superose 6 gel filtration chromatography. Mr standards a–e are as described in FIG. 1. For full details, see the Methods section.

Figure 6:
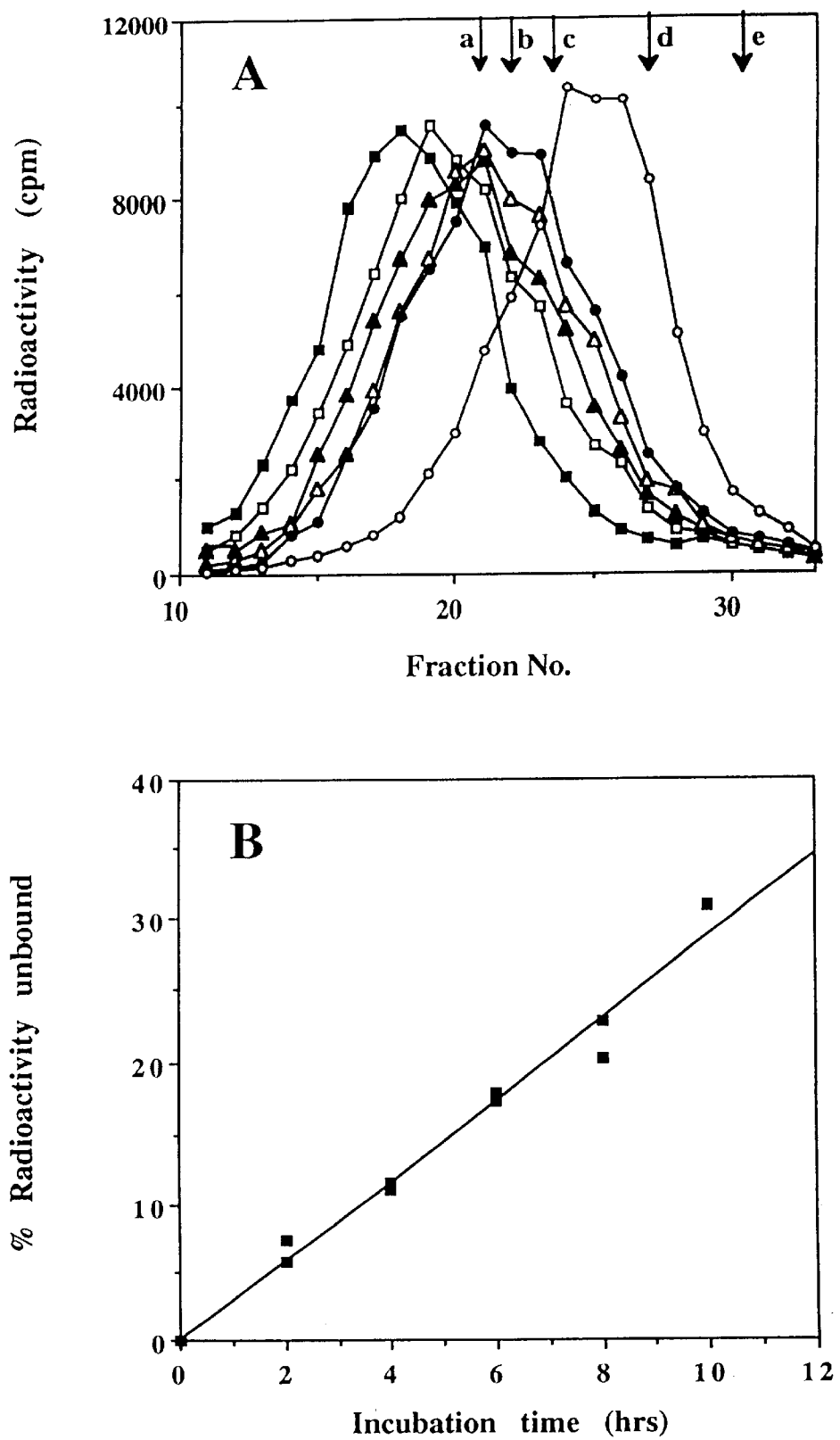

FIG. 6: Degradation of HS as a function of incubation time. HS was incubated with rat 13762 MAT homogenate at pH 5.1 for 2 (□), 4 (▲), 6 (Δ), 8 (●) and 10 hr (○) and in the absence of added enzyme for 4 hr (■) at 37° C. The incubation mixtures were divided and fractionated by A) Sepharose 6 gel filtration chromatography and B) binding to a cHRG-Sepharose column where the unbound fraction was determined for each time point. Mr standards a–e are as described in FIG. 1. For full details, see the Methods section.

Figure 7:
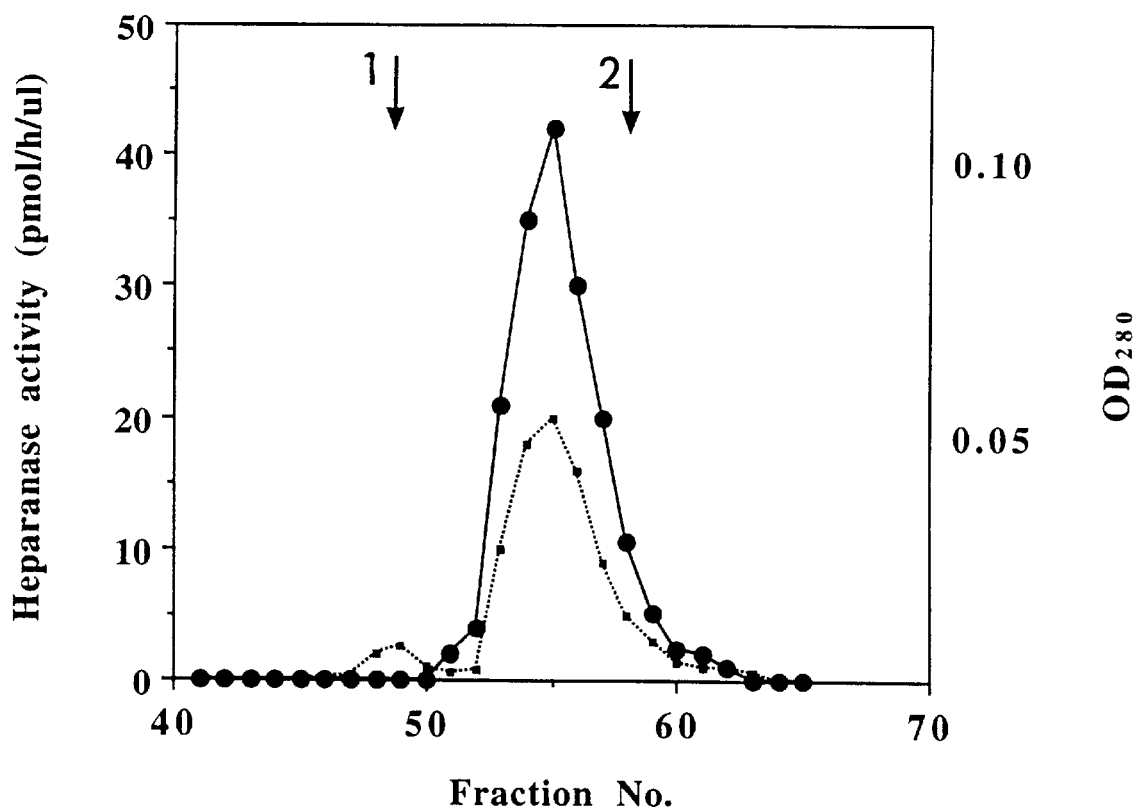

FIG. 7: Superose 12 chromatography of human platelet heparanase. Platelet heparanase from Step 4 was purified by gel filtration as described in the Method section. Fractions were assayed for heparanase activity (○) and monitored for protein ($A_{280}$). Arrows 1 and 2 indicate Ve for bovine serum albumin and ovalbumin respectively.

Figure 8:
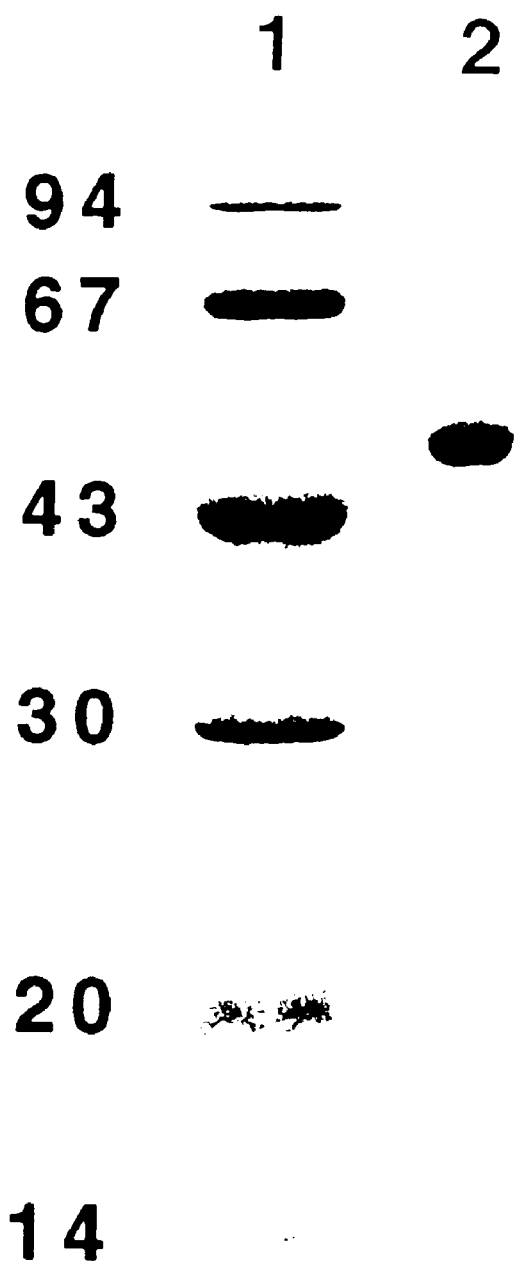

FIG. 8: SDS-PAGE of purified human platelet heparanase. Step 5 purified platelet heparanase was reduced with dithioerythritol and electrophoresed in a 10% polyacrylamide gel. For experimental details, see the Methods section. Lane 1, Mr standards; lane 2, Step 5 heparanase.

EXAMPLE 1

Abbreviations used: bFGF, basic fibroblast growth factor; BSA, bovine serum albumin; cHRG, chicken histidine-rich glycoprotein; CNBr, cyanogen bromide; CR-HS, carboxyl-reduced heparan sulphate; ECM, extracellular matrix; GIcA, glucuronic acid; GIcNAc, N-acetylated glucosamine; GIcNS, N-sulphated glucosamine; GIcNS3S, glucosamine N,3-disulphate; hHRG, human histidine-rich glycoprotein; HRG, histidine-rich glycoprotein; HS, heparan sulphate; HSPG, heparan sulfate proteoglycan; HUVEC, human umbilical vein endothelial cells; IdoA2S, iduronic acid 2-sulphate; NAM, N-acetylmannosamine; PBS, phosphate buffered saline.

I—Materials

Heparin-derived molecular mass ($Mr_{ave}$) standards of 16.7, 10.6, 6.7 and 3.1 kDa were a generous gift from Nova Nordisk (Gentofte, Denmark) (see Kristensen et al, 1991). Porcine mucosal HS (ORG 553) was a generous gift from Organon Int. Bv, (Oss, The Netherlands). Pharmacia Fine Chemicals (Uppsala, Sweden) supplied PD-10 columns, DEAE-Sepharose and cyanogen bromide activated-Sepharose 4B. Sigma Chemical Co. (St Louis, Mo.) supplied crystalline bovine serum albumin, bovine lung heparin, chondroitin ABC-lyase, hydrazine hydrate and hydrazine sulphate. $^3$H-Acetic anhydride (500 mCi/mmol) in toluene solution was obtained from Amersham International (Sydney, Australia). Beckmann (Gladesville, Australia) supplied Ready Safe scintillation fluid. Dowex AG50W-X8 (100–200 mesh; H+form) was obtained from Bio-Rad Laboratories (Richmond, Calif.).

The following cell lines were cultured and harvested as previously described: the metastatic human colonic carcinomas HCT 116 (Schlechte et al, 1989) and KM 12 SM (Morikawa et al, 1988); the metastatic murine melanoma B16-ISF10, the highly metastatic 13762 MAT and DMBA-8A rat mammary adenocarcinoma, and their non-metastatic variants J-clone and DMBA-Sask (Parish et al, 1992); human umbilical vein endothelial cells and the macrophage cell line U937 (Bartlett et al, 1995); human smooth muscle, human lung fibroblasts and human keratinocyte cell line (KJD). Human platelets were obtained by the method of Bartlett et al, (1995). The murine Lewis lung carcinoma (metastatic (D122) and non-metastatic (LLC) variant) and the murine lung carcinoma cell lines (metastatic (A3a) and non-metastatic (SP1) variant) were generous gifts from Dr. James W. Dennis, Samuel Lunenfeld Research Institute, Mount Sinai Hospital, Toronto, Canada and Dr. Lea Eisenbach, Department of Immunology, The Weizmann Institute of Science, Rehovot, Israel respectively. Cell pellets from these cell lines were supplied frozen (–80° C.) by Dr Robin Anderson, Peter MacCallum Cancer Institute, Melbourne, Australia. Cell homogenates were prepared by suspending $10^6$ cells or $10^8$ platelets (which had been previously washed in normal saline) in 0.2 ml of 0.1% (v:v) aqueous Triton X-100 and disrupting by freezing and thawing three times in a solid-$CO_2$/ethanol mixture.

Freshly excised livers from 10 week old Fischer F344 rats were homogenised in 3 volumes (w:v) of 15 mM-dimethylglutarate buffer, pH 6.0, containing 0.5M-NaCl using a polytron homogeniser. Serum and both tumorigenic and adjacent normal lung tissue from human cancer patients was obtained frozen (–80° C.) from the Royal North Shore Hospital, Sydney, Australia. The tissue was thawed and homogenised as described above. Frozen serum from cancer patients and healthy volunteers was thawed and dialysed for 16 h at 4° C. against normal saline. Protein concentrations were estimated by a Bio-Rad Coomassie protein assay kit (Bio-Rad Laboratories, Richmond, Calif.) using BSA as a standard.

II—Methods

Radiolabelled heparan sulphate: Crude porcine intestinal mucosal heparan sulphate ORG553 (100 mg) was dissolved in 2 ml $H_2O$, dialysed for 4 h against 2 l of normal saline and for 16 h against 2 l $H_2O$ at 4° C. in dialysis tubing with a 10 kDa cut-off. The dialysed solution was mixed with 2 ml of 0.1M-Tris.HCl, pH 8.0, containing 0.1 mg/ml BSA and 2 units of chondroitin ABC-lyase, and incubated at 37° C. for 16 h. Following dialysis at 4° C. for 16 h against 2l PBS, the solution was applied to a DEAE-Sepharose column (1.0×6.0 cm) equilibrated in PBS. The column was washed successively with 12 ml each of PBS and 0.3M-NaCl before being eluted with 10 ml of 2M-NaCl which was subsequently lyophilized. The solid was dissolved in the minimum amount of $H_2O$, and desalted using a Pharmacia PD-10 column. The eluant appearing ahead of the NaCl (detected by addition of a drop of a 20% silver nitrate solution) was lyophilized to yield 33 mg of purified heparan sulphate.

The purified heparan sulphate (26 mg) was dissolved in hydrazine hydrate (1 ml) containing hydrazine sulphate (20 mg) and the mixture heated at 100° C. for 2 h in a capped glass vial. The mixture was cooled and dried under a stream of nitrogen. Toluene (1 ml) was added, the mixture dried and this procedure repeated twice more. The residue was dissolved in 2 ml of 1M-NaCl, desalted on a PD-10 column and the desalted material passed through a Dowex 50X-8 (Na+ form) column (1.0×6.0 cm) which was washed with a further 10 ml $H_2O$. The combined flow through and washings were lyophilized to yield 19 mg of partially de-N-acetylated heparan sulphate.

The de-N-acetylated heparan sulphate (19 mg) was dissolved in 1 ml of 0.5M-$NaHCO_3$, containing 10% (v:v) methanol, cooled to 0° C. in an ice bath and 0.1 ml of $^3H$-acetic anhydride (5 mCi, 500 mCi/mmol) in toluene added, and the mixture stirred vigorously for 3 h at 0° C. A further 0.05 ml methanol, 0.1 ml $Na_2CO_3$ and 0.05 ml acetic anhydride were added with stirring for 30 min at 0° C. This procedure was repeated twice more, checking the pH remained alkaline before the mixture was acidified to pH4.0 with acetic acid. After the mixture was warmed to 22° C., the toluene was removed under a stream of nitrogen and the solution desalted on a PD-10 column equilibrated and developed in 10% (v:v) aqueous ethanol. Radioactive material appearing ahead of the $^3H$-acetate peak was lyophilized to yield 21 mg of radiolabelled heparan sulphate which was dissolved in 10% (v:v) aqueous ethanol at a concentration of 2 mg/ml and stored at −20° C.

Histidine-rich glycoprotein-Sepharose: Chicken histidine-rich glycoprotein (cHRG) was prepared from chicken plasma by phosphocellulose ion exchange chromatography (Rylatt et al, 1981). The purity of the preparation was demonstrated by SDS-PAGE where a single Coomassie Blue stained band with a molecular mass of 135 kDa was detected. The material was concentrated to a protein concentration of 2 mg/ml, dialysed against PBS and stored at −20° C. until use.

Bovine lung heparin (50 mg) was dissolved in 10 ml of 0.5M-$NaHCO_3$ containing 10% (v:v) methanol and cooled to 4° C. before 5 aliquots of 0.04 ml acetic anhydride was added at 5 min intervals. The pH was kept above 8.0 with 1M-$Na_2CO_3$. The mixture was stirred for a further 30 min before the acetylated heparin was dialyzed for 16 h at 4° C. against 5 l of 1M-$NaHCO_3$ containing 0.15M-NaCl (coupling buffer).

cHRG (10 mg) was dialysed for 16 h at 4° C. against 2l of coupling buffer and mixed at 4° C. for 30 min with the acetylated heparin solution prepared above to prevent coupling of the HS-binding site of cHRG to the Sepharose beads. Cyanogen bromide (CNBr)-activated Sepharose 4B (2 g) was swollen in 50 ml of 1 mM-HCl for 30 min and washed with 150 ml of 1 mM-HCl in a scintered funnel under vacuum before being washed with 20 ml of coupling buffer. The washed CNBr-Sepharose was immediately added to the heparin-cHRG solution and gently mixed for 24 h at 4° C. A 4 ml solution of 2M-ethanolamine in coupling buffer (adjusted to pH 8.0 with 1M-HCl) was added and gently mixed for a further 16 h. The slurry was poured into a chromatography column (1.5×5.0 cm) and washed successively at 4° C. with 50 ml each of coupling buffer, 0.05M-Tris-HCl buffer, pH 8.0, containing 2M-NaCl and finally PBS. cHRG-Sepharose was stored in PBS at 4° C. Coupling yielded a concentration of 0.8 mg protein bound per ml of beads, which bound 6.2 and 3.1 nmol of radiolabelled lung heparin and HS respectively.

Heparanase assay: cHRG-Sepharose beads (0.2 ml bed column) were placed in disposable 1 ml syringes tamped with glass wool and the mini-columns placed in 10 ml centrifuge tubes standing in an ice bucket. The columns were pre-washed with 1 ml PBS before use. All column procedures were performed on ice.

To assay for heparanase activity, up to 2 μl of sample was added to an incubation mixture consisting of 90 pmol of radiolabelled HS in 0.05M-sodium acetate buffer, pH 5.1, containing 5 mM-N-acetylmannosamine and 0.1 mg/ml BSA in a total volume of 20 μl and incubated at 37° C. for the appropriate time. The reaction was stopped by freezing the tubes, 0.3 ml cold PBS added, the solution centrifuged if necessary at 4° C. and 0.1 ml of the sample applied to a cHRG-Sepharose mini-column pre-equilibrated in PBS. The columns were washed with 0.7 ml PBS, the washings and flow through material transferred to a scintillation vial, 10 ml of scintillation fluid added, and the radioactivity determined. Enzyme activity was expressed as pmol product formed per hour per mg protein or $10^6$ cells or ml of serum. The cHRG-Sepharose columns were regenerated by the addition of 1 ml of 0.05M-Tris-HCl buffer, pH 7.5, containing 2M-NaCl and then equilibrated with PBS.

Heparanase activity was also detected by gel filtration chromatography of the incubation mixture on a Superose 6 HR 10/30 column (Pharmacia LKB Biotechnology, Uppsala, Sweden), equilibrated in and subsequently developed in PBS. The Pharmacia FPLC system was run at a flow rate of 0.25 ml/min with 0.5 ml fractions collected directly into scintillation vials, to which 3 ml of scintillation fluid was added, and the radioactivity determined. The column was calibrated with $^3H$-N-acetylglucosamine (221 Da), bovine lung heparin (12.5 kDa) and heparin-derived Mr ave. standards (16.7, 10.6, 6.7 and 3.1 kDa) which had been partially de-N-acetylated and re-N-acetylated with $^3H$-acetic anhydride as described above for the preparation of radiolabelled HS. Radiolabelled chondroitin-6-sulphate and carboxyl-reduced HS (prepared by the method of Karamanos et al, (1988)) were also prepared by the above method.

Binding of HS to cHRG-Sepharose; Samples in 200 μl of PBS were applied to a mini-column (0.5×4.0 cm) of cHRG-Sepharose equilibrated in PBS at 4° C. The column was washed with 2 ml of PBS and eluted with a linear gradient (2×10 mls) of PBS and 10 mM-sodium phosphate buffer, pH7.2, containing 1.2M-NaCl developed at 0.5 ml/min with 0.5 ml fractions collected directly into scintillation vials, to which 4 ml of scintillation fluid was added and the radioactivity determined. The columns were re-equilibrated in PBS for further use.

III—Results and Discussion
Preparation of a Radiolabelled Heparanase Substrate Previous studies of heparanase activity towards heparin or HS have utilized linking reagents to permit radio-iodination (Oosta et al, 1982) which could mask potential cleavage sites, or acetylation of previously de-N-sulphated HS or heparin with radiolabelled acetic anhydride (Nakajima et al, 1986a). However, as was reported, the latter method affected both the apparent Mr of the substrate, and generated heparanase susceptible linkages in heparin, which had previously been shown to be resistant to murine B16 melanoma heparanase activity (Nakajima et al, 1986a). To ensure the production of a radiolabelled, biologically active, natural substrate for the determination of heparanase activity in a variety of biological samples, purified porcine mucosal HS was partially de-N-acetylated and re-N-acetylated with $^3H$-acetic anhydride to a specific activity of 1650 to 2000 cpm/pmol, which is up to 100 times that previously reported for $^{14}C$ labelled HS (Nakajima et al, 1986a). This labelling procedure has the major advantage that there is no introduction of new or altered cleavage sites into the substrate. The substrate was stored at −20° C. in 10% (v:v) aqueous ethanol where the substrate was stable for over a year without the production of appreciable degradation products despite repeated freezing and thawing. Porcine mucosal HS which has previously been isolated by Hahnenberger et al (1993) has been shown to have a Mr ave of 22 kDa and to contain heparitinase resistant saccharides of dp 2 to 16, enriched in IdoA2S-GlcNS sequences which mediate bFGF activity (Walker et al, 1994). It also contains extended nitrous acid resistant (GlcNAc-containing) sequences of dp 6 to 14–16 (J. E. Turnbull, unpublished observations) and therefore contains alternating sulphated and non-sulphated regions typical of HS species.

Analysis of Heparanase Digestion of the HS Substrate

Before a new heparanase assay could be developed, it was essential that the radiolabelled HS be validated as an appropriate substrate using conventional gel filtration to separate and characterise the degradation products. It was also important to define the degradative properties of the heparanase enzymes used in this study. Heparanase degradation of the radiolabelled substrate was assessed using the highly invasive rat mammary adenocarcinoma 13762 MAT and human platelet homogenates, since the tumour and platelet-derived enzymes have previously been shown to have different substrate specificities, degrading either HS only, or both heparin and HS respectively (Nakajima et al, 1988). To prevent subsequent exo-enzyme degradation of the heparanase degradative products, 5 mM-N-acetylmannosamine (NAM) was added to the incubation mixture to inhibit release of $^3$H-labelled N-acetylglucosamine residues following α-N-acetylglucosaminidase activity (Hopwood and Elliott, 1982).

HS was incubated with 13762 MAT cell homogenate in the presence of NAM at pH 4.2, 5.1, 6.5 and 7.5 for 16 h at 37° C. and the reaction mixture was analysed by gel permeation chromatography (FIG. 1). The sizes of the heparanase-derived products were compared to a series of radiolabelled heparin-derived Mr standards. HS was maximally degraded at pH 5.1 to fragments with an apparent Mr of 5 kDa, compared to apparent Mr of 8 and 16 kDa at pH 6.5 and 7.5 respectively. The rate of degradation at pH 4.2 was slower than at pH 6.5, with a less obvious stepwise breakdown to products. Prolonged incubation of HS with 13762 MAT cell homogenate for 40 h again resulted in incomplete degradation at pH 6.5 and 7.5 (data not shown). To determine if different enzyme activities were present or that different cleavage sites were generated at the higher pH values, the individual products of degradation at pH 5.1, 6.5 and 7.5, following a 16 h-incubation, were collected, desalted and incubated at either pH 5.1 or 6.5 with fresh homogenate for a further 16 h. In each case, each of the tested fragments were degraded to a minimum size of 5 kDa (data not shown). Application of the 5 kDa products of heparanase digestion to DEAE-Sepharose resulted in all of the radioactivity remaining bound, even in the presence of 0.3M-NaCl, indicating that all the HS fragments resulting from heparanase digestion contained highly sulphated HS domains.

A time course incubation of 13762 MAT cell homogenates with HS at pH 5.1 for periods of 2, 4 and 16 h again demonstrated an apparent stepwise degradation of HS (FIG. 2), with three apparent cleavages from 22 to 16 to 8 and finally to 5 kDa. No activity was detected towards chrondroitin-6-sulphate or towards carboxyl-reduced HS (CR-HS) following incubation for 16 h at pH 5.1, 6.5 or 7.5 (results not shown). Human platelet homogenate heparanase activity similarly did not act on CR-HS but digested HS to fragments of 5 kDa, which were retained by DEAE-Sepharose in 0.3M-NaCl. Homogenates from a variety of cell lines, including the highly metastatic human colonic carcinoma HCT 116 and KM 12-SM lines, human umbilical vein endothelial cells (HUVEC), mouse melanoma B16-F10 cells and a rat liver extract were all demonstrated by gel filtration analysis to hydrolyse HS to fragments of 17, 8 and finally 5 kDa during the course of a 16 h incubation (results not shown), indicating that the heparanase activities in each cell lines were cleaving HS to similarly sized products. Previously human platelet, HUVEC, lymphocyte, neutrophil and leukocyte heparanase activities towards bovine endothelial ECM-bound HSPG were also shown to result in the formation of similarly sized HS digestion end products (Vlodavsky et al, 1992).

Incubation of extracts of the highly metastatic rat 13762 MAT and DMBA-8A cell lines and the non metastatic variants J-clone and DMBA-Sask with HS resulted in complete degradation of the HS to 5 kDa fragments by the 13762 MAT and DMBA-8A heparanase activities, whereas the J-clone and DMBA-Sask extracts only partially degraded HS to fragments with apparent Mr of 8 and 17 kDa respectively (FIG. 3). The highly metastatic 13762 MAT and DMBA-8A cell lines were previously shown to be more effective in their ability to degrade the artificial basement membrane Matrigel than the J-clone and DMBA-Sask variants in a basement membrane permeability assay (Parish et al, 1992), thus confirming the correlation of metastatic potential with heparanase activity (Nakajima et al, 1983).

Therefore, porcine mucosal HS is proposed as a suitable natural substrate for the detection of heparanase activity in a variety of cell types, platelets and tissue extracts, and for assessing the heparanase content and the metastatic potential of tumour cell lines. However, due to the multiplicity of cleavage sites the use of gel filtration as a method of separation of products from the undigested substrate makes it difficult to accurately quantify heparanase activity, particularly as multiple cleavages need to occur to allow separation of substrate from product. In addition, it is not known whether the relative rate or each of the cleavages is similar or whether the initial products of digestion may inhibit further cleavage by product inhibition, resulting in a lack of linearity of the assay with respect to time which has been observed for most of the HS degrading exo-activities studied (Freeman and Hopwood, 1986, 1987, 1989a, 1989b). The lack of quantification of the heparanase activity combined with the time and labour required to analyse a single sample by gel filtration analysis highlights the need for a rapid, quantitative heparanase assay capable of detecting a minimum number of substrate cleavages.

Development of a Quantitative Heparanase Assay

The interaction of HS- and heparin-binding proteins such as antithrombin III, acidic and basic fibroblast growth factor (FGF), platelet factor 4, β-thromboglobulin and histidine-rich glycoprotein (HRG) with HS has been well documented (Jackson et al, 1991) along with more recent attempts to define their binding motifs on the HS molecule following chemical (primarily nitrous acid degradation) or bacterial heparanase and heparitinase digestion (Turnbull and Gallagher, 1990, 1991; Tumbull et al, 1992; Walker et al, 1994). However, apart from the demonstration that mammalian heparanase can release active bFGF from the ECM (Ishai-Michaeli et al, 1990), little work has been published on the interaction of HS-binding proteins with HS following mammalian heparanase degradation.

While investigating the interaction of chicken HRG (cHRG), an abundant plasma-derived HS-binding protein, with HS it was observed that not only did cHRG mask the mammalian MAT cell heparanase cleavage sites on HS chains, but following heparanase cleavage of HS, the cHRG-binding motif on HS was lost. Therefore, following heparanase digestion, cleaved HS fragments bound less efficiently to cHRG-coupled Sepharose beads, enabling the development of an efficient and novel method of separating the HS substrate from the products of heparanase digestion.

When HS was applied to a cHRG-Sepharose column and eluted by a salt gradient at pH 7.2, the relatively weakly binding HS was eluted by 0.27M-NaCl (FIG. 4) compared to lung heparin which was eluted by 0.6M-NaCl (results not shown). However, the 5 kDa fragments following complete digestion of HS by a 13762 MAT cell homogenate did not bind to cHRG-Sepharose. When HS was then degraded by 13762 MAT cell heparanase using the standard assay at pH 5.1 for 2, 4 and 16 h, the assay mixture was divided into 3 and analysed by gel filtration chromatography, binding to DEAE-Sepharose and binding to cHRG-Sepharose. Gel filtration analysis yielded a similar profile to FIG. 1 with products at 17, 8 and 5 kDa respectively. The application of the assay mixture, and the subsequent elution of radiolabelled HS products from the cHRG-Sepharose column by a salt gradient, demonstrated that the decrease in the apparent Mr of the HS fragments by gel filtration correlated with an increase in material not binding to cHRG-Sepharose (FIG. 4) indicating that the HRG-binding motif on HS was lost following heparanase digestion. There was no apparent change in the affinity of the bound HS fragments towards the cHRG-Sepharose column over the period of the incubation. The binding of HS to cHRG-Sepharose (and the apparent Mr of HS during gel filtration analysis) was not influenced by the assay blanks containing buffer only, 0.1 mg/ml BSA, heat inactivated enzyme or active enzyme chromatographed with HS at 4° C. (data not shown). Following application of the incubation mixtures to DEAE-Sepharose, all radioactivity remained bound in the presence of 0.3M-NaCl indicating that the products of digestion were not due to desulphation by some endo-sulphatase activity (Bartlett et al, 1995; Dawes and Pepper, 1992; Wells and Dawes, 1995).

To investigate whether the binding of HS to HRG occurs at or in the vicinity of a heparanase sensitive cleavage site, HS was digested with 13762 MAT cell homogenate in the absence and in the presence of a 3:1 molar ratio of cHRG:HS (HS appears to have 3 potential cleavage sites, each of which may bind to a HRG molecule). FIG. 5 shows that in the presence of cHRG, the rate of degradation of HS (resulting in the formation of small (5 kDa) fragments) was significantly retarded compared to cleavage in the absence of cHRG where the substrate was completely degraded.

Determination of Heparanase Activity

Using the cHRG-Sepharose assay, maximal heparanase activity was observed at pH 5.1 (results not shown), similar to previous assays analysed by gel filtration (FIG. 1). NAM was added to the incubation mixture to inhibit exoglycosidase release of $^3$H-GlcNAc which would not bind to cHRG-Sepharose. The affinity of HS and the digestion products for cHRG-Sepharose was not influenced by the incubation mixtures containing final concentrations of 0.1 mg/ml BSA, 0.1% (v:v) Triton X-100 or up to 0.2M-NaCl. However, tissue homogenate heparanase activity was increased up to 2-fold when assayed in the presence of 0.1% Triton X-100. In contrast, soluble heparanase activity (following removal of the membranes by centrifugation) was unaffected by the addition of BSA or Triton X-100 to the incubation mixture, although highly purified enzyme preparations required the presence of BSA in the incubation mixture for optimal activity and stability. The requirement of BSA for the determination of optimal activity of highly purified enzyme and Triton X-100 for maximal activity of tissue homogenates has been extensively reported for the determination of HS-degrading exo-enzyme activities (Freeman and Hopwood, 1986, 1987, 1989a, b, 1992). The cHRG-Sepharose columns were routinely eluted by high salt concentrations, and re-equilibrated in PBS. The columns were stored in PBS at 4° C. and were in constant use for over a 2 year period without appreciable decrease in binding capacity.

FIG. 6 compares the change in apparent Mr following 13762 MAT homogenate heparanase digestion of HS (FIG. 6A), with the appearance of unbound radioactive HS fragments following application of the incubation mixture to cHRG-Sepharose (FIG. 6B). Gel filtration analysis of material not bound to cHRG-Sepharose following a 6 h incubation showed an apparent Mr of 17 kDa (results not shown). Enzyme activity determined by cHRG-Sepharose analysis was linear with respect to time for up to 10 h incubation and for up to 30% conversion substrate to product (FIG. 6B). Following prolonged (24 h) incubation, 84% of the radioactivity passed through the cHRG-Sepharose column and had an apparent Mr of 5 kDa. Material remaining bound to the column presumably contained higher affinity HRG-binding motifs or was heparanase resistant, a phenomenon which was not investigated. Background material not binding to cHRG-Sepharose was generally of low Mr, being less than 6 kDa, and may represent previously cleaved HS fragments obtained during isolation of the HS from the porcine mucosa. The fragments may be removed by prior affinity purification of the HS substrate using cHRG-Sepharose, or by prior gel filtration to remove the smaller Mr species.

Human HRG (hHRG)-Sepharose can be used satisfactorily in place of cHRG-Sepharose for the determination of heparanase. However, the binding affinity of hHRG for BALB/c 3T3 cell surface HSPG was weaker than that observed for cHRG (Brown and Parish 1994) and this was reflected by a higher affinity of cHRG-Sepharose for porcine mucosal HS than that observed for hHRG-Sepharose (results not shown). Chicken HRG has the additional advantage that it can be purified in higher yield from plasma than hHRG (C. Parish, unpublished observations). Commercially available bovine kidney HS (Mr 17 kDa) can be used in place of porcine intestinal HS for the determination of heparanase activity. In contrast, commercial bovine intestinal HS cannot be used for the determination of heparanase activity as it has a Mr less than 5 kDa, and is essentially not mammalian heparanase sensitive by both gel filtration and cHRG-Sepharose analysis.

Analysis of Heparanase Activity in Different Biological Samples

A variety of cell lines, tissues and platelet homogenates as well as serum from normal and cancer patients were tested for heparanase activity using the quantitative cHRG-Sepharose heparanase assay. Table 1 shows that the heparanase activity present in homogenates of the highly metastatic rat mammary adenocarcinoma 13762 MAT and DMBA-8A cell lines was 4- and 10-fold higher than for the respective non-metastatic J-clone and DMBA-Sask variants. These values closely correlate with both the relative ability of these cell lines to degrade an artificial (Matrigel) basement membrane (Parish et al, 1992) and for the cell homogenates to degrade HS as assessed by gel filtration analysis (see earlier). The metastatic variants of the murine Lewis lung carcinoma (D122) and lung carcinoma (A3a) degraded HS 2.5- and 4.8-fold faster than their respective non-metastatic variants (Table 1). Previously, Nakajima et al, (1986a, b) had reported only a 1.5- to 2.2-fold difference in heparanase activity between extracts of the poorly metastatic B16-F1 sub-line compared to the more highly metastatic B16-BL6, -F10 and -B16b sub-lines using their solid phase assay with deN-sulfated, reN-acetylated HS.

The sensitivity of the heparanase assay of the present invention may be of use for the clinical assessment of cancer patients. Heparanase activity was determined in lung tumour tissue taken from six lung carcinoma patients. Of these, heparanase activity in the primary tumour of five patients was elevated from 2- to 4-fold compared to that from the patient's adjacent non-tumourous lung tissue (results not shown). Although heparanase activity was barely detectable in human plasma (less than 4 pmol/hr/ml plasma), significant heparanase activity was detected in normal adult sera and in sera from patients with metastatic malignancies. Serum heparanase activity in the cancer patients tested was 2-fold higher than that observed for normal controls (229.7±28.8 (n=8) for cancer patients compared to 116.6±13.3 (n=5) pmol/hr/ml serum for controls), confirming the results observed for sera from malignant melanoma patients (Nakajima et al, 1988). In fact, these authors observed a 4-fold increase in serum heparanase activity in patients where tissue metastases were present. Nakajima et al (1986c, 1988) also observed that heparanase serum levels in rats were 17-fold higher than normal 30 days after injection of the highly metastatic 13762NF mammary adenocarcinoma cells while enzyme activities in the sera of rats bearing MTLn3 tumours correlated well with the extent of the metastases.

Heparanase activity was also detected in a variety of human and rat cell lines, platelets and tissue homogenates (Table 2) which should represent valuable sources of the heparanase enzyme for future purification. For ease of comparison between cells and tissues heparanase activity is expressed/mg of protein extracted. The development of this rapid, and quantitative heparanase assay will be invaluable for the purification of heparanase activity from a variety of sources and will enable the rapid screening of putative heparanase inhibitors.

TABLE 1

Heparanase activity of metastatic and non-metastatic tumour cell lines Tumour cell homogenate heparanase activity was assessed following fractionation of the incubation mixture on cHRG-Sepharose. Enzyme activity is expressed as mean ± SEM for three separate experiments except where otherwise designated. For full details, see the Methods section.

| Tumour type | Cell line | Metastatic | Heparanase activity (pmol/hr/$10^6$ cells) |
|---|---|---|---|
| Rat mammary adenocarcinoma | 13762 MAT | Yes | 47.4 ± 2.2 |
|  | 13762 MAT (j-clone) | No | 12.8 ± 0.5 |
|  | DMBA-8A | Yes | 35.6 ± 3.2 |
|  | DMBA-Sask | No | 3.4 ± 0.1 |
| Human colonic carcinoma | HCT 116 | Yes | 10.3, 10.4 |
| Human monocyte | U937 | No | 7.6, 8.2 |
| Human keratinocyte | KJD | No | 7.8, 10.2 |
| Murine Lewis lung carcinoma | D122 | Yes | 16.4 ± 1.1 |
|  | LLC | No | 6.5 ± 0.5 |
| Murine lung carcinoma | A3a | Yes | 16.3 ± 1.2 |
|  | SP1 | No | 3.4 ± 0.2 |

TABLE 2

Heparanase activity in human and rat cells and tissues. The range of heparanase activity in a variety of homogenates of human and rat tissue and cultured cells was assessed following fractionation of the incubation mixture on cHRG-Sepharose. For full details, see the Methods section.

| Cell or tissue | Heparanase activity (pmol/hr/mg protein) |
|---|---|
| Human platelets | 2178–3591 (n=6) |
| Human colonic carcinoma (HCT 116) | 38.2–66.6 (n=4) |
| HUVECS | 21.0–42.6 (n=4) |
| Human smooth muscle cells | 50.3, 75.9 |
| Human lung fibroblasts | 1.5, 3.0 |
| Human keratinocyte (KJD) | 62.2, 78.4 |
| Rat 13762 MAT cells | 141.1–349.2 (n=6) |
| Rat liver | 9.5–28.3 (n=6) |

EXAMPLE 2

Abbreviations Used

BSA bovine serum albumin; cHRG, chicken histidine-rich glycoprotein; HRG, histidine-rich glycoprotein; HS, heparan sulphate; HSPG, heparan sulphate proteoglycan; HUVEC, human umbilical vein endothelial cells; PBS, phosphate buffered saline.

I—Materials

Heparin-derived molecular mass ($Mr_{ave}$) standards of 16.7, 10.6, 6.7 and 3.1 kDa were a generous gift from Nova Nordisk (Gentofte, Denmark) (see Kristensen et al, 1991). Porcine mucosal HS (ORG 553) was a generous gift from Organon Int. Bv,(Oss, The Netherlands). Pharmacia Fine Chemicals (Uppsala, Sweden) supplied concanavalin A-Sepharose 4B, chelating-Sepharose 4B, Superose 6 and 12 HR 10/30 gel chromatography columns, molecular mass standard kits for standardising gel filtration columns and SDS-PAGE gels, and octyl-Sepharose. Sigma Chemical Co. (St Louis, Mo.) supplied crystalline bovine serum albumin (BSA), bovine lung and porcine mucosal heparin, bovine kidney HS, 3,3-dimethyl glutaric acid, Blue A-agarose, octyl-agarose, CHAPS, zinc acetate, Amicon Corp. (Beverly, Mass.) supplied Centricon 100 and 30 microconcentrators. Beckmann (Gladesville, Australia) supplied Ready Safe scintillation fluid. Stratagene USA (La Jolla, Calif.) supplied StrataClean Resin.

Expired platelet-rich plasma was obtained from the Canberra Hospital, washed twice with normal saline by centrifuging the suspended platelets at 1600×g for 15 min at 20° C. and the pellet stored frozen at −80° C. Human platelets were also obtained by the method of Bartlett et al (1995) and washed twice in normal saline. Cell homogenates were prepared by suspending $10^8$ platelets in 0.2 ml of 0.1% (v:v) aqueous Triton X-100 and disrupting by freezing and thawing three times in a solid-$CO_2$/ethanol mixture. Protein concentrations were estimated by a Bio-Rad Coomassie protein assay kit (Bio-Rad Laboratories, Richmond, Calif.) using BSA as a standard.

II—Methods

Preparation of Radiolabelled Substrates

Radiolabelled porcine intestinal mucosal heparan sulphate (ORG 553), porcine intestinal mucosal and bovine lung heparin were prepared by the method of Example 1 by N-deacetylation with hydrazine and N-acetylation with $^3$H-acetic anhydride.

Heparanase Assays

Assay 1

Human platelet heparanase activity was determined towards HS and the products separated from the substrate using the chicken histidine-rich glycoprotein (cHRG)-Sepharose beads separation method of Example 1. Up to 2 µl of sample was added to an incubation mixture consisting of 90 pmol of radiolabelled HS in 0.05M-sodium acetate buffer, pH 5.1, containing 5 mM-N-acetylmannosamine and 0.1 mg/ml BSA in a total volume of 20 µl and incubated at 37° C. for the appropriate time to yield between 5 and 20% breakdown of the substrate to products. The reaction was stopped by freezing the tubes, 0.3 ml cold phosphate-buffered saline (PBS) added, the solution centrifuged if necessary at 4° C. and 0.1 ml of the sample applied to a cHRG-Sepharose mini-column (0.2 ml) pre-equilibrated in PBS. The columns were washed with 0.7 ml PBS, the washings and flow through material transferred to a scintillation vial, 10 ml of scintillation fluid added, and the radioactivity determined. Enzyme activity was expressed as pmol product formed per hour per mg protein.

Assay 2

Heparanase activity towards 2 µg of the radiolabelled HS or heparin analogues was assayed as described above for 16 h at 37° C., and detected by gel filtration analysis of the incubation mixture on either Superose 6 (for HS degradation) or Superose 12 (for heparin degradation). The chromatography columns were both equilibrated in and developed with PBS at a flow rate of 0.25 ml/min with 0.5 ml fractions being collected directly into scintillation vials, to which 3 ml of scintillation fluid was added, and the radioactivity determined. The columns were calibrated with $^3$H-N-acetylglucosamine (221 Da), bovine lung heparin (12.5 kDa) and heparin-derived $Mr_{ave}$. standards (16.7, 10.6, 6.7 and 3.1 kDa) which had been partially de-N-acetylated and re-N-acetylated with $^3$H-acetic anhydride as described above for the preparation of radiolabelled HS.

Purification of Platelet Heparanase

All procedures were performed at 4° C. unless otherwise stated. Heparanase activity towards HS was determined using assay 1. In each step (except for the 0.8M-NaCl wash of Blue A-agarose in Step 3), the buffer washes of the columns continued until no more protein was detected in the column eluate using a Bio-Rad protein assay.

Step 1. Solubilisation of enzyme activity: Fifty units of frozen, washed human platelets were allowed to thaw by suspension in 4 volumes of 15 mM-sodium dimethylglutarate buffer, pH 6.0, containing 0.5M-NaCl (buffer A), and the sample freeze/thawed three times following immersion in a solid $CO_2$/ethanol bath. The suspended platelet homogenate was centrifuged at 35000×g for 60 min and the supernatant used in Step 2. The pelleted material was resuspended in 200 ml of buffer A, freeze/thawed once again and centrifuged as before. This procedure was repeated twice more before the final pellet was homogenised in buffer A containing 1% (v:v) CHAPS and centrifuged as before. Heparanase activity in the CHAPS supernatant was purified exactly as described below except for the addition of Triton X-100 to the extract in Step 2.

Step 2. Concanavalin A-Sepharose chromatography: The supernatant from Step 1 was made 0.2% in Triton X-100 (v:v) and applied at approximately 1 ml/min to a concanavalin A-Sepharose column (1.5×5.0 cm) equilibrated in buffer A containing 0.2% Triton X-100 (buffer B). The column was washed in turn with 25 ml of buffer B and 40 mls of buffer A at 4° C. before being washed with 40 ml of buffer A which had been prewarmed to 20° C. Heparanase activity was eluted by the application of 40 ml of buffer A containing 20% α-methyl mannoside (w:v), which had been prewarmed to 20° C. The eluate was collected into a container held in an ice bucket.

Step 3. $Zn^{2+}$-chelating Sepharose/Blue A-agarose chromatography: The enzyme solution from Step 2 was applied at 1 ml/min to a $Zn^{2+}$-chelating Sepharose column (1.0× 10.0 cm) connected in series with a Blue A-agarose column (1.0×2.0 cm). The combined columns were washed with 50 ml of buffer A, before the disconnected Blue A-agarose column was washed in turn with 20 ml of Tris buffer (60 mM-Tris/HCl buffer, pH 7.4, made up in 10% (v:v) glycerol) containing 0.5M-NaCl, and 1.5 ml of Tris buffer containing 0.8M-NaCl.

Step 4. Blue A-agarose/octyl-agarose chromatography: The Blue A-agarose column in Step 3 was connected to an octyl-agarose column (1.0×1.5 cm) which wass equilibrated in Tris buffer containing 2M-NaCl. The Blue A-agarose column was eluted at 0.5 ml/min by 15 ml of Tris buffer containing 2M-NaCl. The octyl-agarose eluate was immediately concentrated to 5 ml in volume in an Amicon ultrafiltration s tirred cell containing a PM10 membrane before being concentrated to 0.2 ml in volume by Centricon 30 centrifugation. Buffer A containing 10% (v:v) of glycerol (buffer C) was added and the enzyme solution concentrated again to 0.4 ml.

Step 5. Superose 12 chromatography: The concentrated enzyme solution from Step 4 was applied in two separate lots of 200 µl to two Superose 12 HW 10/30 columns connected in series and equilibrated in and developed with buffer C at 0.5 ml/min. Fractions of 0.5 ml were collected assayed for heparanase activity and fractions containing heparanase activity were concentrated to 0.4 ml by Centricon 30 centrifugation. The purified enzyme was stable for months when stored in buffer C at 4° C.

Step 6. Centricon 100 and 30 centrifugation: For platelet preparations obtained from less than 20 units of washed platelets, the 2M-NaCl eluate from the octyl-Sepharose column in Step 4 was concentrated by centrifugation in a Centricon 100 microconcentrator and the filtrate containing the heparanase activity was concentrated and dialysed against buffer C using a Centricon 30 microconcentrator as described in Step 4.

Native and Subunit Mr

The native Mr of purified human platelet heparanase activity was determined by chromatography on two Superose 12 HW 10/30 columns connected in series as described in Step 5 above. The columns were calibrated with the following Mr standards: thyroglobulin (669 kDa), ferritin (440 kDa), catalase (232 kDa), fructose-biphosphate aldolase (158 kDa), bovine serum albumin (67 kDa), ovalbumin (43 kDa), chymotrypsinogen (25 kDa) and ribonuclease A (13 kDa).

Discontinuous SDS-PAGE were run according to the method of Laemmli (1981) and stained with Coomassie Brilliant Blue R250. The 10% polyacrylamide gels were calibrated with the following Mr standards: phosphorylase b (94 kDa), bovine serum albumin (67 kDa), ovalbumin (43 kDa), carbonic anhydrase (30 kDa), soya-bean trypsin inhibitor (20 kDa) and α-lactalbumin (14 kDa). Samples were concentrated by the addition of 10 ul of StrataClean Resin, vortexing and centrifuging the suspension according to the manufacturer's instructions. The pelleted material was reduced by boiling in dithiothreitol, and the suspension applied to the stacking gel by the standard procedure.

III—Results and Discussion
Purification of Platelet Heparanase

Previously, it has been shown that human platelet homogenates contained 2.2–3.6 nmol/h/mg protein heparanase activity towards HS, a 60-fold higher activity compared to that observed in the metastatic human colonic carcinoma tumour cell line HCT 116 (Example 1). Therefore platelets are an extremely rich source of mammalian heparanase activity. Heparanase activity can be released from freshly obtained platelets by thrombin-induced degranulation (Hoogewerf et al, 1995), but it has been observed that the level of heparanase activity released by thrombin stimulation of out of date platelets was quite variable. Therefore heparanase activity was obtained by solubilisation by the freeze/thawing of previously frozen washed platelets.

Because of the reported instability of the enzyme (Oldberg et al, 1980) and the relatively low recoveries of activity obtained during purification of the enzyme (Hoogewerf et al, 1995; Oosta et al 1982), chromatography conditions were developed to maximise the concentration of the eluted protein. This was achieved by batch (or isocratic) rather than gradient elution, and devising conditions where the enzyme would pass unbound through one column to be bound by the next column in series. This allowed a saving in the time taken to assay for the enzyme activity following a salt gradient elution and minimised the loss of activity due to dilution of the enzyme.

Homogenisation of the previously frozen washed platelets in buffer A (which contained 0.5M-NaCl) did not release any appreciable soluble enzyme activity. Approximately 75% of the total heparanase activity, however, was solubilized by repeated freeze/thawing of the platelets followed by centrifugation of the homogenate (Table 3). The remaining membrane associated enzyme could only be released by homogenisation in buffer A containing 10% (v:v) CHAPS. Homogenisation of the membranes with buffer A containing 10% Triton X-100 solubilised the enzyme, but it rapidly lost activity. The membrane bound enzyme was purified from 50 units of washed platelets by the same procedure used to isolate the soluble enzyme.

All of the enzyme activity applied to the concanavalin A-Sepharose column was tightly bound when applied in the presence of detergent. Washing the column by application of buffer A at 20° C. removed more non-specifically bound protein than by washing the column at 4° C. alone. The recovery of enzyme activity and speed of elution (in less than five column volumes of eluant) was greatly enhanced by elution of the column at 20° C., compared to the normal elution at 4° C. Heparanase activity was purified by 19-fold with a recovery of 56% from the original platelet supernatant (Table 3). The recovery of enzyme activity from this Step was generally in the range of 55 to 70%. No further heparanase activity was eluted from the column by buffer containing α-methylmannoside and 0.1% Triton X-100 at 20° C. The use of chelating-Sepharose and dye-matrix chromatography, which has been so successfully used to purify HS-degrading exo-enzyme activities (Bielicki et al, 1990; Clements, et al 1985; Freeman and Hopwood, 1986, 1987, 1989), has not been previously used to isolate mammalian heparanase activity. The enzyme, which did not bind to the zinc-helating column, was tightly bound to the dye column which permitted a complete separation of the heparin-degrading exo-enzyme activities α-L-iduronidase, β-D-glucuronidase and α-N-acetylglucosaminidase from the platelet heparanase (results not shown). No heparanase activity was detected in the unbound fraction, or in the low salt (0.5 and 0.8M-NaCl) Tris buffer washes of the dye column. High salt (2M-NaCl) elution of heparanase from the Blue A-agarose column resulted in most of the contaminating protein binding to the octyl-agarose column, while the unbound heparanase was concentrated in an almost pure form for a final purification by gel chromatography. Whereas the enzyme did not bind to octyl-agarose, it did bind to octyl-Sepharose when applied in 2M-NaCl, but was eluted from the column in 1M-NaCl (results not shown). Heparanase activity was purified a further 80-fold over step 2, giving an overall purification of 1500-fold with a recovery of 26% of activity. No further activity was recovered from the chelating-Sepharose column or from the octyl-agarose column following elution of the rest of the bound protein from the columns with buffer A containing 0.1M-imidazole and 1% Triton X-100 respectively. Furthermore, no heparanase activity was detected in the filtrate following Centricon 30 concentration of the almost pure enzyme in contrast to that reported by Hoogewerf et al (1995).

Gel filtration chromatography (FIG. 7) resulted in a final 1.1-fold purification of the enzyme over Step 4, resulting in a final 1900-fold purification with 19% recovery of activity from the original homogenate. This compares with a 240000-fold purification in 5.6% yield and a 4100-fold purification in 8% yield from plateiet-rich plasma reported by Oosta et al (1982) and Hoogewerf et al (1995) respectively. Smaller preparations of the purified human platelet heparanase (using less than 20 units of washed platelets), could be prepared within 2 days in up to 30% yield using the method described in this Example. In this case, proportionally smaller columns are used and the gel filtration Step 5 replaced by filtering the octyl-agarose eluate through a Centricom 100 to be concentrated by a Centricom 30 filter. The membrane associated enzyme was also purified with 25% recovery of enzyme activity with a specific activity of 6600 nmol/h/mg of protein, similar to that observed for the soluble enzyme. The membrane associated form of the enzyme exhibited the same chromatographic properties as the soluble form of the enzyme.

Native Molecular Mass

Gel filtration analysis of both purified heparanase (see FIG. 7) and of enzyme obtained following concanavalin A-Sepharose chromatography (Step 2) demonstrated that the enzyme has an apparent Mr of 50 kDa. No enzyme activity was detected in either case at Mr values corresponding to 8–10 kDa or dimers or tetramers of the chemokine sized platelet heparanase activity as reported by Hoogewerf et al (1995), nor was any activity detected that corresponded to an apparent Mr of 134 kDa as reported by Oosta et al (1982). The results presented in this Example, however, are similar to the Mr value of 40–60 kD obtained by Graham and Underwood (1996) for human platelet extracts. This value is also similar to the 45 kDa native Mr reported for purified human placental heparanase (Gilat et al, 1995) and 50 kDa reported for partially purified human spleen heparanase (Sewell et al, 1989), but differs from the Mr value of 94 kDa reported for the murine melanoma enzyme (Jin et al, 1990). Furthermore, purified human heparanase was not retained by Centricon 100 kDa membranes, but was retained by Centricon 30 kDa membranes. No heparanase activity was detected in the 30 kDa membrane filtrate as reported by Hoogewerf et al (1995). However, following Step 2 chromatography, enzyme activity was retained by Centricon 100 kDa membranes indicating substantial interaction with other proteins during the process of concentration since the Step 2 material had an apparent Mr of 50 kDa by gel filtration analysis (results not shown). SDS-PAGE analysis of the purified enzyme indicated a single Coomassie blue staining band corresponding to a Mr value of 50 kDa under both reducing (FIG. 8) and non-reducing conditions (results not shown), which was identical to the value obtained by gel filtration analysis. The purified membrane associated enzyme also had a native Mr and subunit Mr of 50 kDa as determined by gel filtration and SDS-PAGE analysis (under reducing conditions). It is not known how the enzyme is associated with the membrane. Because its size is similar to the soluble enzyme, it is possible that heparanase may exist in both soluble and membrane associated forms similar to the lysosomal enzyme acid phosphatase, which is transported to the lysosome by a mannose6-phosphate independent pathway, and which has a 2 kDa C-terminal transmembrane peptide which results in the enzyme existing in the lysosome as both a membrane bound and soluble forms. (Peters et al, 1990). Previously, Gallagher et al (1988) reported the presence of a rat liver membrane heparanase activity. However, unlike the enzyme reported here, that enzyme was inactive at pH values less than 7.5.

Substrate Specificity of Purified Platelet Heparanase

Purified human platelet heparanase activity towards HS, as determined by assay 1, was maximal at pH 5.1 similar to that reported for the platelet homogenate heparanase activity (Example 1). The purified enzyme cleaved both HS and heparin following analysis of the assay by gel filtration. Porcine mucosal HS (22 kDa), and bovine kidney HS (17 kDa) were each cleaved to 5 kDa fragments as reported for platelet homogenate heparanase activity towards the mucosal HS (Example 1). Previously, porcine mucosal HS was shown to be cleaved in a stepwise fashion from 22 to 17 to 11 and finally to 5 kDa fragments (Example 1).

Mucosal heparin and the more highly sulphated lung heparin were each cleaved from 12.5 kDa to 4 and 6 kDa fragments respectively . Mucosal heparin appeared to be cleaved twice in a stepwise fashion compared to the singularly cleaved lung heparin. Unlike the report of Hoogewerf et al (1995), however, there was no evidence of the production of the predominately disaccharide products resulting from the cleavage of HS or heparin (or modified heparins) following prolonged incubations of either purified enzyme or Step 1 homogenate heparanase, even after pre-treatment of the enzyme with reducing and oxidising agents as described by those authors.

TABLE 3

Purification of Heparanase from Human Platelets.

| Step | Heparanase activity (nmol/h) | Total Protein (mg) | Specific activity (nmol/h/mg) | Purification (-fold) | Yield (%) |
|---|---|---|---|---|---|
| 1. Homogenate | 12192 | 3465 | 3.52 | — | — |
| Supernatant | 9892 | 2098 | 4.72 | 1 | 100.0 |
| Pellet | 4480 | 552 | 8.12 | (1.7) | — |
| 2. Concanavalin A-Sepharose | 5523 | 63.1 | 87.53 | 18.5 | 55.8 |
| 3. Zn-Sepharose/ Blue A-agarose/ | | | | | |
| 4. Octyl-agarose | 2579 | 0.37 | 6970.3 | 1476.7 | 26.1 |
| 5. Superose 12 | 1873 | 0.24 | 7804.2 | 1653.4 | 18.9 |

REFERENCES

Bar-Ner, M., Kramer, M. D., Schirrmacher, V., Ishai-Michaeli, R., Fuks, Z., and Vlodavsky, I. (1985). *Int. J. Cancer* 35, 483–491.

Bar-Ner, M., Mayer, M., Schirrmacher, V., and Vlodavsky, I. (1986). *J. Cell. Physiol.* 128, 299–306.

Bartlett, M. R., Cowden, W. C. and Parish, C. R. (1995a). *J. Leukocyte. Biol.* 57, 207–213.

Bartlett, M. R., Underwood, P. A., and Parish, C. R. (1995b). *Immunol. Cell Biol.* 73, 113–124.

Benezra, M., Vlodavsky, I., and Bar-Shavit, R. (1992). *Exp. Cell. Res.* 201, 208–215.

Bielicki, J., Freeman, C., Clements, P. R. and Hopwood, J. J. (1990). *Biochem. J.* 271, 75–86.

Brenan, M., and Parish, C. R. (1986). *Eur. J. Immunol.* 16, 423–430.

Brown, K. J., and Parish, C. R. (1994). *Biochemistry* 33, 13918–13927.

Castellot Jr., J. J., Favreau, L. V. Karnovsky, M. J. and Rosenberg, R. D. (1982) *J. Biol. Chem.* 257, 11256–11260.

Clements, P. R., Brooks, D. A., Saccone, G. T. P. and Hopwood, J. J. (1985). *Eur. J. Biochem.* 152, 21–28.

Coombe, D. R., Parish, C. R., Ramshaw, I. A. and Snowden, J. M. (1987). *Int. J. Cancer,* 39, 82–88.

Crissman, J. D., Hatfield, J., Shaldenbrand, M., Sloane, B. F. and Honn, K. V (1985). *Lab. Invest.* 53, 470–478.

Dawes, J., and Pepper, D. S. (1992). *Thromb. Haem.* 67, 468–472.

Eldor, A., Bar-Ner, M., Yahalom, J., Fuks, Z. and Vlodavsky, I. (1987). *Sem. Thromb. Haem.* 13, 475–488.

Freeman, C., and Hopwood, J. J. (1986). *Biochem. J.* 234, 83–92.

Freeman, C., and Hopwood, J. J. (1987). *Biochem. J.* 246, 355–365.

Freeman, C., and Hopwood, J. J. (1989a). *Anal. Biochem.* 176, 244–248.

Freeman, C, and Hopwood, J. J. (1989b). *Biochem J.* 259, 209–216.

Freeman, C., and Hopwood, J. J. (1991). *Biochem. J.* 279, 399–405.

Freeman, C., and Hopwood, J. J. (1992). *Biochem. J.* 282, 605–614

Gallagher, J. T., Walker, A., Lyon, M., and Evans, W. H. (1988). *Biochem. J.* 250, 719–726.

Gamse, G., Fromme, H. G. and Kresse, H. (1978). *Biochim. Biophys. Acta.* 544, 514–528.

Gilat, D., Hershoviz, R., Goldkorn, I., Cahalon, L., Vlodavsky, I. and Lider, O. J. (1995). *J. Exp. Med.* 181, 1929–1934.

Godder, K., Vlodavsky, I., Eldor, A., Weksler, B. B., Haimovitz-Freidman, A., and Fuks, Z. (1991). *J. Cell. Physiol.* 148, 274–280.

Graham, L. D., Hayward, I. P. and Underwood, P. A. (1995a). *Biochem. Mol. Biol. Int.* 37, 231–237.

Graham, L. D., Mitchell, S. M. and Underwood, P. A. (1995b). *Biochem. Mol. Biol. Int.* 37, 239–246.

Graham, L. D. and Underwood, P. A. (1996). *Biochem. Mol. Biol. Int.* 39, 563–571.

Hahnenberger, R., Jakobsen, Å. M., Ansari, A., Wehler, T., Svahn, C. M. and Lindahl, U. (1993). *Glycobiology* 3, 567–573.

Hennes, R., Frantzen, F., Keller, R., Schirrmacher, V. and Schwartz-Albiez, R. (1988). *Br. J. Cancer.* 58, 186–188.

Hoogewerf, A. J., Leone, J. W., Reardon, I. M., Howe, W. J., Asa, D., Heinrikson, R. L., and Ledbetter, S. R. (1995). *J. Biol. Chem.* 270, 3268–3277.

Hopwood, J. J., and Elliott, H. (1982). *Clin. Chim. Acta.* 120, 77–86.

Höök, M., Wasteson, Å., and Oldberg, Å. (1975). *Biochem. Biophys. Res. Commun.* 67, 1422–1428.

Irimura, T., Nakajima, M., and Nicolson, G. L. (1986). *Biochemistry* 25, 5322–5328.

Ishai-Michaeli, R., Eldor, A., and Vlodavsky, I. (1990). *Cell Regul.* 1, 833–842.

Jackson, R. L., Busch, S. J. and Cardin, A. D. (1991). *Physiol. Rev.* 71, 481–539.

Jin, L., Nakajima, M. and Nicolson, G. L. (1990). *Int. J. Cancer.* 45, 1088–1095.

Karamanos, N. K., Hjerpe, A., Tsegenidis, T., Engfeldt, B., and Antonopoulos, C. A. (1988). *Anal. Biochem.* 172, 410–419.

Klein, U., and von Figura, K. (1976). *Biochem. Biophys. Res. Commun.* 73, 569–576.

Klein, U., and von Figura, K. (1979). *Hoppe-Seyler's Z. Physiol. Chem.* 360, 1465–1471

Kristensen, H. I., Tromborg, E. M., Nielsen, J. R., Nielsen, J. I., Johansen, K. B. and Ostergaard, P. B. (1991). *Thromb. Res.* 64, 131–141.

Laemmli, U. K. (1970). *Nature* (London) 227, 680–685.

Lane, D. A., Pejler, G., Flynn, A. M., Thompson, E. A., and Lindahi, U. (1986). *J. Biol. Chem.* 261, 3980–3986.

Laskov, R., Ishai-Michaeli, R., Sharir, H., Yefenof, E., and Vlodavsky, I. (1991). *Int. J. Cancer* 47, 92–98.

Lider, O., Baharav, E., Mekori, Y. A., Miller, T., Naparstek, Y., Vlodavsky, I., and Cohen, I. R. (1989). *J. Clin. Invest.* 83, 752–756.

Matzner, Y., Bar-Ner, M., Yahalom, J., Ishai-Michaeli, R., Fuks, Z., and Vlodavsky, I. (1985). *J. Clin. Invest.* 76, 1306–1313.

Matzner, Y., Vlodavsky, I., Bar-Ner, M., Ishai-Michaeli, R., and Tauber, A. I. (1992). *J. Leukoc. Biol.* 51, 519–524.

Morikawa, K., Walker, S. M., Nakajima, M., Pathak, S., Jessup, J. M. and Fidler, I. J. (1988). *Cancer Res.* 48, 6863–6871.

Nakajima, M., Irimura, T., Di Ferrante, D., Di Ferrante, N., and Nicolson, G. L. (1983). *Science* 220, 611–613.

Nakajima, M., Irimura, T., and Nicolson, G. L. (1986a). *Anal. Biochem.* 157,162–171.

Nakajima, M., Irimura, T., and Nicolson, G. L. (1986b). *Cancer Lett.* 31, 277–283.

Nakajima, M., Welch, D. R., Irimura, T., and Nicolson, G. L. (1986c). *Prog. Clin. Biol. Res.* 212, 113–122.

Nakajima, M., Irimura, T., and Nicolson, G. L. (1988). *J. Cell. Biochem.* 36, 157–167.

Naparstek, Y., Cohen, I. R., Fuks, Z., and Vlodavsky, I. (1984). *Nature* 310, 241–243.

Oldberg, Å, Heldin, C-H., Wasteson, Å., Busch, C., and Höök, M. (1980). *Biochemistry* 19, 5755–5762.

Oosta, G. M., Favreau, L. V., Beeler, D. L., and Rosenberg, R. D. (1982). *J. Biol. Chem.* 257, 11249–11255.

Parish, C. R., Jakobsen, K. B., and Coombe, D. R. (1992). *Int. J. Cancer* 52, 378–383.

Parish, C., Willenborg, D., and Cowden, W. (1990). *Today's Life Sci.* 2, 20–27.

Peters, C., Braun, M., Weber, B., Wendland, M., Schmidt, B., Pohlmann, R., Waheed, A. and von Figura, K. (1990) *EMBO J.* 9, 3497–3506.

Ricoveri, W., and Cappelletti, R. (1986). *Cancer Res.* 46, 3855–3861.

Rylatt, D. B., Sia, D. Y., Mundy, J. P., and Parish, C. R. (1981). *Eur. J. Biochem.* 119, 641–646.

Schlechte, W., Murano, G., and Boyd, D. (1989). *Cancer Res.* 49, 6064–6069.

Schmitt, M., Janicke, F., and Graeff, J. (1992). *Fibrinolysis* 6, (Suppl 4), 3–26.

Sewell, R. F., Brenchley, P. E. G., and Mallick, N. P. (1989). *Biochem. J.* 264, 777–783.

Thunberg, L., Bäckström, G., Wasteson, Å., Robinson, H. C., Ögren, S., and Lindahl, U. (1982). *J. Biol. Chem.* 257, 10278–10282.

Turnbull, J. E., and Gallagher, J. T. (1990). *Biochem. J.* 265, 715–724.

Turnbull, J. E., and Gallagher, J. T. (1991). *Biochem. J.* 273, 553–559.

Turnbull, J. E., Fernig, D. G., Ke, Y., Wilkinson, M. C., and Gallagher, J. T. (1992). *J. Biol. Chem.* 267, 10337–10341.

Vlodavsky, I., Eldor, A., Haimovitz-Friedman, A., Matzner, Y., Ishai-Michaeli, R., Lider, O., Naparstek, Y., Cohen, I. R., and Fuks, Z. (1992). *Invasion Metastasis* 12, 112–127.

Vlodavsky, I., Ishai-Michaeli, R., Bar-Ner, M., Fridman, R., Horowitz, A. T., Fuks, Z., and Biran, S. (1988). *Isr. J. Med. Sci.* 24, 464–470.

Walker, A., Turnbull, J. E., and Gallagher, J. T. (1994). *J. Biol. Chem.* 269, 931–935.

Wasteson, A., Glimelius, B., Busch, C., Westermark, B., Heldin, C-H. and Norling, B. (1977). *Thromb. Res.* 11, 309–321.

Wasteson, A., Hook, M. and Westermark, B. (1976). *FEBS Letters,* 64, 218–221.

Wells, X. E., and Dawes, J. (1995). *Thromb. Haem.* 74, 667–672.

Willenborg, D. O., and Parish, C. R. (1988). *J. Immunol.* 140, 3401–3405.

Yahalom, J., Eldor, A., Biran, S., Fuks, Z. and Vlodavsky, I. (1985). Radiother. Oncol. 3, 211–225.

Yahalom, J., Eldor, A., Fuks, Z. and Vlodavsky, I. (1984) *J. Clin. Invest.* 74, 1842–1849.

Yurchenco, P. D., and Schittny, J. C. (1990). FASEB J. 4, 1577–1590.

What is claimed is:

1. A method for the purification of human platelet heparanase, which method comprises the steps of:

i. homogenizing human platelets in a CHAPS-containing solution to obtain heparanase-containing material;

ii. contacting the heparanase material with a Concanavalin A-Sepharose chromatography matrix in the presence of Triton X-100 to bind heparanase activity to said matrix;

iii. eluting a first purified heparanase-containing fraction from said matrix;

iv. contacting said first purified heparanase-containing fraction with a $Zn^{2+}$-chelating Sepharose chromatography matrix;

v. contacting effluent from said $Zn^{2+}$-chelating Sepharose chromatography matrix with a dye-resin matrix to bind heparanase activity to said dye-resin matrix, wherein said dye-resin matrix comprises a Blue A-resin or Reactive Red-resin matrix;

vi. eluting a second purified heparanase-containing fraction from said dye-resin matrix;

vii. contacting the second purified heparanase-containing fraction with an octyl-agarose matrix to remove contaminating proteins; and viii. purifying heparanase from effluent from said octyl-agarose matrix by gel filtration chromatography.

2. A method according to claim 1, wherein the resin in said dye-resin matrix comprises agarose, Sepharose or acrylamide.

3. A method according to claim 1, wherein said gel filtration chromatography comprises Superose 12 chromatography.

4. Substantially purified human platelet heparanase prepared by the method of claim 1.

5. Substantially purified human platelet heparanase prepared by the method of claim 1 characterised in that i. it has a native molecular mass (Mr) of about 50 kDa when analysed by gel filtration chromatography and by SDS-PAGE; and ii. it degrades both heparin and heparan sulphates.

6. Substantially purified human platelet heparanase according to claim 5, characterised in that it degrades bovine lung and porcine mucosal heparin from 12 kDa to 6 and 4 kDa fragments respectively, and porcine mucosal heparan sulphate in a stepwise fashion from 22 kDa to 5 kDa fragments, by gel filtration analysis.

* * * * *